United States Patent
Harayama et al.

(10) Patent No.: US 10,370,687 B2
(45) Date of Patent: Aug. 6, 2019

(54) GENETICALLY MODIFIED STRAIN OF EUKARYOTIC MICROALGA HAVING IMPROVED TRIGLYCERIDE PRODUCTIVITY, AND USE THEREOF

(71) Applicants: CHUO UNIVERSITY, Tokyo (JP); DENSO CORPORATION, Aichi (JP)

(72) Inventors: Shigeaki Harayama, Tokyo (JP); Yoko Ide, Tokyo (JP); Jun Abe, Tokyo (JP); Yuki Kasai, Tokyo (JP); Norihide Kurano, Kariya (JP)

(73) Assignees: CHUO UNIVERSITY, Tokyo (JP); DENSO CORPORATION, Aichi (JP)

( * ) Notice: Subject to any disclaimer, the term of this patent is extended or adjusted under 35 U.S.C. 154(b) by 0 days.

(21) Appl. No.: 15/756,233

(22) PCT Filed: Sep. 2, 2016

(86) PCT No.: PCT/JP2016/075875
§ 371 (c)(1),
(2) Date: Feb. 28, 2018

(87) PCT Pub. No.: WO2017/038993
PCT Pub. Date: Mar. 9, 2017

(65) Prior Publication Data
US 2018/0245112 A1 Aug. 30, 2018

(30) Foreign Application Priority Data
Sep. 2, 2015 (JP) .................................. 2015-173161

(51) Int. Cl.
| | | |
|---|---|---|
| *C12N 1/12* | (2006.01) | |
| *C12P 7/64* | (2006.01) | |
| *C12N 9/10* | (2006.01) | |
| *C12N 9/16* | (2006.01) | |
| *C12N 9/24* | (2006.01) | |
| *C12N 15/52* | (2006.01) | |
| *C12N 9/26* | (2006.01) | |

(52) U.S. Cl.
CPC .......... *C12P 7/6463* (2013.01); *C12N 9/1029* (2013.01); *C12N 9/16* (2013.01); *C12N 9/2402* (2013.01); *C12N 9/2408* (2013.01); *C12N 15/52* (2013.01); *C12P 7/6445* (2013.01); *C12Y 203/0102* (2013.01); *C12Y 301/02014* (2013.01); *C12Y 302/0102* (2013.01)

(58) Field of Classification Search
CPC ........................ C12N 9/1029; C12Y 203/0102
USPC ...................................................... 435/257.1
See application file for complete search history.

(56) References Cited

U.S. PATENT DOCUMENTS

| | | | |
|---|---|---|---|
| 8,394,614 B2 | 3/2013 | Roberts et al. | |
| 8,722,359 B2 | 5/2014 | Kilian et al. | |
| 8,835,149 B2 | 9/2014 | Coppersmith et al. | |
| 2014/0106417 A1 | 4/2014 | Schneider et al. | |
| 2015/0337255 A1 | 11/2015 | Kurata et al. | |

FOREIGN PATENT DOCUMENTS

| | | |
|---|---|---|
| JP | 2014014334 | 1/2014 |
| JP | 2014117202 | 6/2014 |
| JP | 2015015918 | 1/2015 |

OTHER PUBLICATIONS

Quinn Jason C., et al., "The potentials and challenges of algae based biofuels: a review of the techno-economic, life cycle, and resource assessment modeling", Bioresource Technology, vol. 184, 2015 (pp. 444-452).
Hung Chun-Hsien et al., "Functional study of diacylglycerol acyltransferase type 2 family in Chlamydomonas reinhardtii", FEBS Letters, vol. 587, 2013 (pp. 2364-2370).
Niu Ying-Fang et al., "Improvement of Neutral Lipid and Polyunsaturated Fatty Acid Biosynthesis by Overexpressing a Type 2 Diacylglycerol Acyltransferase in Marine Diatom *Phaeodactylum tricornutum*", Marine Drugs vol. 11, 2013 (pp. 4558-4569).
Xue Jiao et al., "Genetic improvement of the microalga *Phaeodactylum tricornutum* for boosting neutral lipid accumulation", Metabolic Engineering, vol. 27, 2015 (pp. 1-9).
Iskandarov U. et al., "Cloning and characterization of a GPAT-like gene from the microalga *Lobosphaera incisa* (Trebouxiophyceae): Overexpression in Chlamydomonas reihnhardtii enhances TAG production", Journal of Applied Phycology, 2015. DOI 10.1007/s10811-015-0634-1 (33 pages total). pp. 1-32.
Muto Masaki et al., "Enhancement of glycerol metabolism in the oleaginous marine diatom *Fistulifera solaris* JPCC DA0580 to improve triacylglycerol productivity", Biotechnology for Biofuels, vol. 8 (1), 2015. DOI 10.1186/s13068-014-0184-9 (pp. 1-7).
Davis M.S., et al., Overproduction of Acetyl-CoA carboxylase activity increases the rate of fatty acid biosynthesis in *Escherichia coli*, The Journal of Biological Chemistry, vol. 275, 2000 (pp. 28593-28598).
Voelker Toni A., et al., "Alteration of the Specificity and Regulation of Fatty Acid Synthesis pf *Escherichia coli* by Expression of a Plant Medium-Chain Acyl-Acyl Carrier Protein Thioesterase", Journal of Bacteriology, vol. 176, 1994 (pp. 7320-7327).

*Primary Examiner* — Tekchand Saidha
(74) *Attorney, Agent, or Firm* — Lucas & Mercanti, LLP

(57) ABSTRACT

It is an object of the present invention to provide the eukaryotic microalgae, which have been genetically modified such that larger amounts of assimilation products produced by photosynthesis are directed to the synthesis of triglyceride (=triacylglycerol; TAG), and specifically, the present invention relates to a genetically modified strain of eukaryotic microalgae, in which a gene encoding an AGL1 protein is highly expressed, or a gene encoding an FAT1 protein and/or a gene encoding a DGAT2 protein are further highly expressed, as well as the gene encoding an AGL1 protein, wherein TAG productivity is improved in comparison to the parent strain thereof.

9 Claims, 15 Drawing Sheets

Specification includes a Sequence Listing.

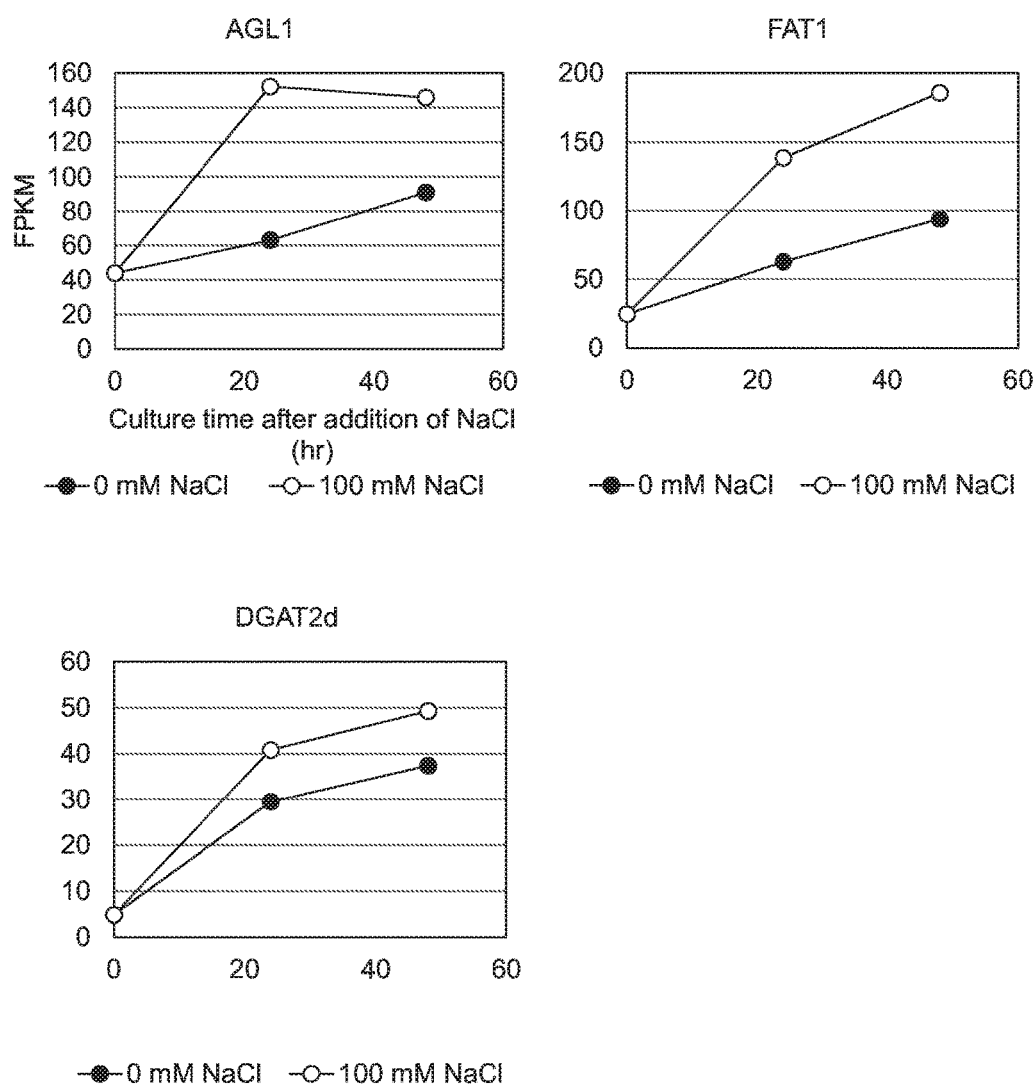

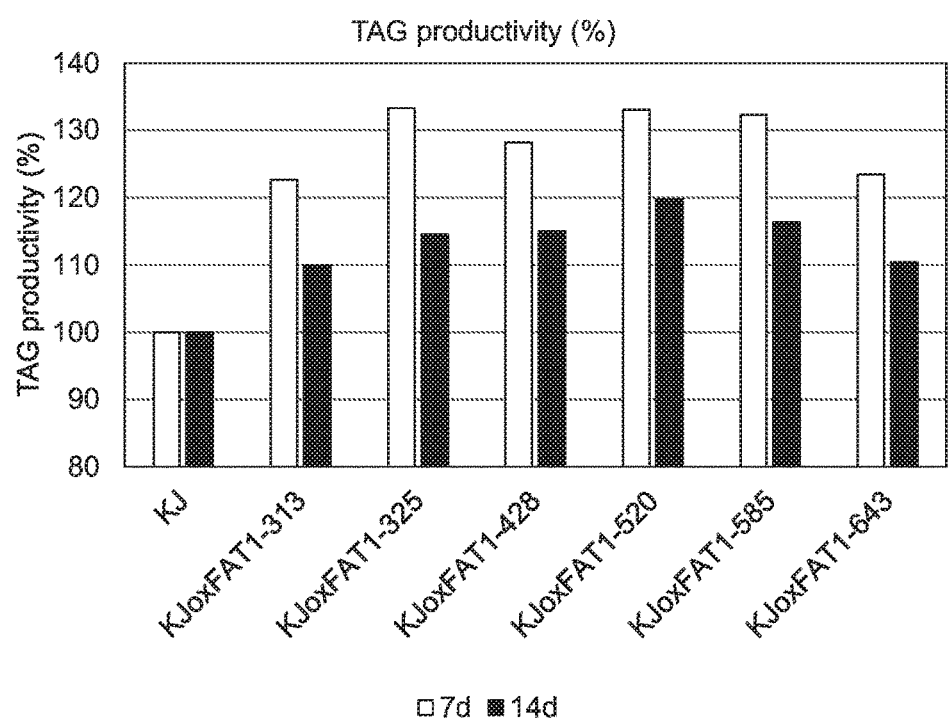

SEQUENCE LISTING

<160> NUMBER OF SEQ ID NOS: 15

<210> SEQ ID NO 1
<211> LENGTH: 7357
<212> TYPE: DNA

<213> ORGANISM: Pseudococcomyxa sp.

<400> SEQUENCE: 1

```
aattggattg tgatcacgtt caacaaagtt tggatctggc ttctaatatg acggacgata      60
ttctgtgcac aaccagtatt tgtcatctgg ctgcaacaaa atttgaagac aagaactttg     120
tgggcaggct ctaattcggc cagctttgag gacgctggca gaggccacct gtaagcacat     180
gctcgtcgtc gagctctcct tcgattgcta agatcggcaa acagacgtgt tcaatcgtac     240
caagatgttg gtctgcaagc tctagcatag cttgcttacc tgtgaacgga ttgtacgcaa     300
gcttgaagtc ggcaggcact tggccaggtt cttcccatca gtcctctatc tgccggtcga     360
gacgagccaa agccagactt ctgtacagtg tcacatcgat cgaaaacata tgtcggcttg     420
cgtctagggt atcagtctcg aggggcacgg taggtggaat taggagtaag tgtcctgatc     480
agacctgtca gcagcgaaga cagcttggcg atcggcgttt ccagacgtcg atggctaacg     540
aggcaaggcg gctagggagg ctgtctgcct catccgccaa gctctgcctg ctggtagtag     600
ccctgagcag cgcgctcgta cgctgccagt caccaggagg gttcggctcc ccacctccag     660
gccaaggcca gtgcgacgct agcgggccca gggtagagtg cggtgcgtct gcgcgtctct     720
tctttggctt ctttcgacaa attttgatct tgaagtacct tgctggacct tctaaagcag     780
ctggcaacct ttgtaccatt tttgtcaggc ccacaacatg cagctcgagc gttttgagcg     840
cgtgcataaa cttgcgtcct cttatagctt atagaactac catgcataca cagagatagc     900
ctgtcatgac atgcgtcatc gaaaaggccg cgttcaatgt gcaagtttag tatatgtgca     960
atattgtcga tggcttcacg agagacggac cataccatgc ttcatgcaca tgtcgtgaga    1020
ttattgctgt aatgcaggat ggaacggcat cgaaagctgg aaatgtgcct ccaagggctg    1080
ctgttatgat cccaacactc ctacccaggt tggcacagcc agtgtgaagg tcacaacacc    1140
cgtgtgtttc aagcctaacg gtggagccag cacatatgac ctctccggag gtttcactgc    1200
agcaggtgtg gtattcaagg caattcttgc ttcggtggcg tgtttgcatg ccatatcagc    1260
acatacaaat gttgcaggaa accatcagaa cttgctccct tttctgacac atgtgctctt    1320
gcgcagccaa tgggaatgga ctacagggca cacttcagca atctggtcct ggatcgcagc    1380
cagaactggg cgcagacatc aagactctga ccattaccgt ggaaaacatc actcctgaca    1440
tattgcatgc aaagattggc gcgccaggac gatgggaagt ccccaaaagc atcttcctga    1500
ctccaaatgt cacaggtagg ggaggatttg ctatatgttt gcacatcagt ggattgcagc    1560
atcatggaat ggatctgatc ttggtcgcca actccttgat tgtgtctgca gcatctaacg    1620
gtccggcaaa ctaccaattc aactacagtg tgtcgcccct cacatttgct gtggctcgcg    1680
caaacaacaa tggtcaggcg ctcttcaaca ctgttggctc tcgtctggtc atgaaggtat    1740
gaattggtca tgttcatttt gaccggcatt tcaacatgac tgctggtttt cctacaagca    1800
catgattaag tcgagcatgc cccatttcac ccgcatgcca gattgtggct tagtattgaa    1860
gcgcccatgg attcacagga ccaatacatg gaaatctcca cctcagtgcc agagactgct    1920
gctctgtatg gccttggcga gcgcacatcc tccactggta tagagctgcg tagagatggc    1980
attcctcttg cactctggaa ccgcgatcac caggcggcct tgcctgatca gaatgtctat    2040
ggctctcacc ctatcctgat ggatgtccgc gaaggtgctg cctccctgat ttgcatgtgc    2100
ctctttgatg cttgctttat tgggtgcatg agataccagt tgtcctgaga aaacagcagg    2160
tcagtcctga tcaaatgttc actgtgttgc agatggcaca gcgcatggtg tgctgctgct    2220
gaacagcaat ggcatggatg tggtgctgac aaagacacga gtgcagtgga gggtccttgg    2280
```

```
tggtgtgttt gacttctact tcttgatggg tccgacccca aatgctgtcc tggatcagct    2340
gaccaccatc atcggccgcc ctgtcatgcc tccatactgg agtttgggcc tgatgaacag    2400
caagtgagcg tgttgtcacc ctgctggcct acgctgtttt gttatcagtg tgttttgttt    2460
atcaatgttg tgacgtgttc tcatgtgagc tgtgccactg agaggtgtca atttgctgca    2520
gatatggtta tggatctgct gagttctacg atcagatcct taatggctat gggaatgcca    2580
gcattccctt ggaaacattt gtgtcagact cacagtacat ggaccacgat caggacttca    2640
cgcttggcag cacattctct cttcctgata tgaaggtatg ttggaccatc aggatgcata    2700
ccttcagtgc cccaggtgtc tttgatttcc atgttgctga tcgggaaatg tttttgcaga    2760
atttcctgaa cagaatcaga gcccaagggc agcgatgggt tccaatcctg acccaaata    2820 ttcacatcaa aaagggtat gcgccttacg acagcggcat caaggcagat atcttcatca    2880
aagatgtttc agggagcccg tatgttggcc aggtacgaag ttttgctgaa cataaatgct    2940
tgcatccgta atttttcctg tctcagtaat gtgatcgaag aatttacaga ctgcatcttt    3000
tctttcaatc ctttccatga cctgatcaca attcttgctc gcagctttgg cctggtgcat    3060
gccattggcc tgacttcaag aaccccaatg caactacttg gtggaccagc cagattaagg    3120
tgctcactca tcttttgcaga ccggtgcaca cttgatgtgg caatgtcttg tcatgccaca    3180
cgcaactgtt agactgccct ccattaggat tgcaagtcct aaatgaagct tatgctgtgc    3240
tgagcagagc gtctacgatg acttggagat ggatggcatc tggattgaca tgaacgagcc    3300
ctcaaattac tgcaccggag atgtctgctg aatgatggt tggtacctcg ttcctgtctt    3360
ttgcagatat cctctgactc cgatggtgca tgagattgga ccatgaccat caccaccaat    3420
tttacccaaa gaatttctgt tctgtacggt atcttacaga gaaggctgct cactctctgc    3480
cttgtcaaca tatgctgcca tgccaggtgc ccaaggaatt tactggtgtt gtgctctttg    3540
cagacactgt gccagcgcgc aatgatttcg tgtgcatgct cggctgcgtc agcggcaagg    3600
accaggtgat ggccacaacc ggcaacaaga gcatcactct caacgaaagc tactttaacc    3660
cgccatacac cattaacaac ggcgacaacg cctacaacat cagctacaag acagtggcag    3720
taacggcata ccactatgac ggcaccttgg tgtacaacgc gcacaacctg tatggcatgc    3780
tggagacgct ggccacaact tctgctctgc agaagctgcg caacaagcgc caattcatcc    3840
taaccaggtg cgaggcacct ttgagctgca tgtgttttgt gggtaatttt ttatgtctgg    3900
tggtgcataa agattcttct cctaatccat ttcgaatcat cacaaggtgc attttcatta    3960
tctgctcttg ggagagcgtg tgaataagtg tgttccggtg gttgctgcga gttcaggtcc    4020
actttcctgg gctctggagc ctatgcagcc cattggaccg gtgacaccaa tgccaagtgg    4080
gaggacatgc gatggtcaat cacaaccgtc ctgaataatg gcattgccgg catctccttc    4140
tctggagcag acatctgcgg gttcatgatg catgccactg atgagctgtg ctcacgctgg    4200
gcagctgttg gtgccttcta cccttacgcc cgcaaccacc attccgatgg ctggcaggag    4260
ttcttcaggt actgactgtg ccgctctctc cagctccgaa gtctcatgct gactgcattt    4320
gttgcaatgc atgccaggaa tgcattcagg acttcatgtg ctgcaaagag gatgcaagct    4380
ttgaagatgt gcctctgtga taggctgtga taggctcatg gcatgcctc acttgctaca    4440 ggtgggagtc cacgtcaata gctgcaagga aggtgttcac gacgcgctac aggctgctgc    4500
cctacctgta caccgctttc tttgactcgc acacctatgg gtgccctgtt gcgcggccac    4560
tgttcttcac cttcccggcg gacaacacca cgcgcagcat ctcagagcag tggatgatgg    4620
```

-continued

```
gcgatgctct gctggtgtct cctatcctct atgagaagac caccacagta aaggcatact    4680
tccccaaggg aacctggtat gacttttaca ccggcagagt tgtcgatgcc tccgctggcg    4740
gcaagtatga cagtgtctcg gtaagtgtaa ccccctagct gtttgccaca aaatttgtgc    4800
tgagcaagag aattgcagga ctgccacttg ctgcatgtgc catgtcagtt gcttctaatg    4860
cattccaatg tgtaatctgg tgccacgatt aggtgctgcg cacctgtgac gacaatccca    4920
tgctattgtg aaggctgagt agtaacaagg tgtatgctgc tctacaggct gacatcactg    4980
acaatgtgcc gctgcatgtc cttggcggca acatcattcc catagctctg ggctcacaat    5040
tcatgctcac ccaagctgtt cgcaacgcca gccatgccct tgttgttgcc ttccccaagg    5100
ccaactccac ttatgcaggt tcgcttgcct ctctgccctg tcctgtatag tttcttgtgt    5160
ttgctacata tcctcatcat atgggagtaa gcttgctgta ttggagttca gaatggtcaa    5220
gggatgagct tcaacttcaa ttcaacttcc catcataagg tctgtgctgt gaatgctgca    5280
ggcgaccggt gcggtggccg atgtggcgga gctccacagg ctggagtgct gaatgcctgt    5340
ggccacatgt accttgacca gggcgaggag ctgaacctgt cacggaacct caacaactac    5400
cttaacctgg catcacagat ggtgcagcag gtaattgttt atgtcacaac tcagcctcaa    5460
tcacaagcat gacacaggga cgcctggaaa gcattcggaa agcatcacaa tgtgctagag    5520
ttgttgcaat gtctcatctg gtggatgata tgcacccaca atatgacatc tgtgtgtgca    5580
ggcgagcggt tcctacaagg gtttcctgag tgcaaccttc gccggcactc ctggcggctc    5640
atctggcgcc acctgcggaa aggatgacag ctggtcgtgg ccggtcattg acactgtcat    5700
tgtcatgggc actggtcctg tagatggcga ttctattgtt gttcaggtgg gttcactgca    5760
ggcccctcaa cgatgccctg ctttgtgtca caaaaggag tgttgtgctt gcagtcaca    5820
cccacgagtg gcgctggttg gctgaaactt cctgatgcat tttgcaggct gtgtcagcat    5880
cgagcacaac tcctggaaca gtgcagacag cgtctgtgga cagcactcca ggcgtcacaa    5940
acctctcaac gggcaccgcc aagtatgacg ccacgctgca gaagctcacc atctccggcc    6000
tgaacttcca gctgacgtgc cccacgggtc tgcgcatcag ctggagcgct ggagcccctt    6060
cagcgcctgc cagcacacca gcagccgcga ccacggccgc ggcagtcttc ggcacgcctg    6120
tcaaggaccc tccctcgccg cccaacagtg tggtctcgcc cccgggggt ggatcgagcc    6180
cgacctccaa tttcgggtcg cccagcagcc cctcttccgg cagttccccg tcacagtcgt    6240
cgtccgctgc gtctcccagt ggcagcagct cttcagggtc gccgtcttct agcagtggct    6300
ctggatcctc cagtggctct gggtctccca gcggctcacc ctacagctcg agtggcagct    6360
ctggctcgcc agctgtctcc agcagcccct caggctccgg cacaccctcg agctctggca    6420
gcccctcatc ctacagcagc tacagcagcc cctcaggcta cggcagctct tcaccttctt    6480
acagcagccc ctcgtcatac agcccctcct catacagcag ctcttcgtac agcccctctt    6540
cgtacagcag ctcgccatcc agctacagca gcagtagcag tcgcagcccc agcccgacct    6600
catcctacta cagccccagc aggagctctt caggaggcgg tggaggtggc cctggggggcg    6660
gtggccctgg aggtggcggc cctggaggcg gtcccttctt tggatgagca agtctgtcct    6720
gggaagtatc cacaatacat tatgctctcc actgagagct gcaccagctg gactggtgcc    6780
aggctgatgc ctaggtgctg gcagcttcct tgaagtaaac atattcattg ctgagcgaga    6840
acatatggag gttgtctcag catctgagag gtgctagaaa tagatgaacc agagaaacag    6900
tagtgaccgt caaaagcttg agactgttcc gagcaaaatg aactgtgatg aagaccactg    6960
ctggactgtg gagcaacagg ctgttgcatg ccaccaatgc agaattcggc ccaaaatgct    7020
```

```
catagagact gtagggttgg tttagcaggg taccaaatga tgagggcaaa ggagggtgga      7080
gccggttgcc cttcctcttg aaggatacca aaacagtagt ccaagacagg attgcacact      7140
ttgcatcagt gacagcttgc ttgccagagc gcgtgctctg tcggtgttgc ttagctgttg      7200
cgaaacactg gcgtgagtga tttctatcta tacgaatgat ttcgtacata ttgtctgaga      7260
gtggcactgt agtattaggc ttgatttcat ttgcgccgcg gtggctttgc agtatactgg      7320
gtatttgatg cttctacaat agaggacatc cgttaca                              7357

<210> SEQ ID NO 2
<211> LENGTH: 3714
<212> TYPE: RNA
<213> ORGANISM: Pseudococcomyxa sp.
<220> FEATURE:
<221> NAME/KEY: CDS
<222> LOCATION: (1)..(3714)

<400> SEQUENCE: 2
```

| | | | | | | | | | | | | | | | | |
|---|---|---|---|---|---|---|---|---|---|---|---|---|---|---|---|---|
| aug | gcu | aac | gag | gca | agg | cgg | cua | ggg | agg | cug | ucu | gcc | uca | ucc | gcc | 48 |
| Met | Ala | Asn | Glu | Ala | Arg | Arg | Leu | Gly | Arg | Leu | Ser | Ala | Ser | Ser | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| aag | cuc | ugc | cug | cug | gua | gua | gcc | cug | agc | agc | gcg | cuc | gua | cgc | ugc | 96 |
| Lys | Leu | Cys | Leu | Leu | Val | Val | Ala | Leu | Ser | Ser | Ala | Leu | Val | Arg | Cys | |
| | | 20 | | | | | 25 | | | | | 30 | | | | |

| | | | | | | | | | | | | | | | | |
|---|---|---|---|---|---|---|---|---|---|---|---|---|---|---|---|---|
| cag | uca | cca | gga | ggg | uuc | ggc | ucc | cca | ccu | cca | ggc | caa | ggc | cag | ugc | 144 |
| Gln | Ser | Pro | Gly | Gly | Phe | Gly | Ser | Pro | Pro | Pro | Gly | Gln | Gly | Gln | Cys | |
| | | | 35 | | | | | 40 | | | | | 45 | | | |

| | | | | | | | | | | | | | | | | |
|---|---|---|---|---|---|---|---|---|---|---|---|---|---|---|---|---|
| gac | gcu | agc | ggg | ccc | agg | gua | gag | ugc | gga | ugg | aac | ggc | auc | gaa | agc | 192 |
| Asp | Ala | Ser | Gly | Pro | Arg | Val | Glu | Cys | Gly | Trp | Asn | Gly | Ile | Glu | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| ugg | aaa | ugu | gcc | ucc | aag | ggc | ugc | ugu | uau | gau | ccc | aac | acu | ccu | acc | 240 |
| Trp | Lys | Cys | Ala | Ser | Lys | Gly | Cys | Cys | Tyr | Asp | Pro | Asn | Thr | Pro | Thr | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cag | guu | ggc | aca | gcc | agu | gug | aag | guc | aca | aca | ccc | gug | ugu | uuc | aag | 288 |
| Gln | Val | Gly | Thr | Ala | Ser | Val | Lys | Val | Thr | Thr | Pro | Val | Cys | Phe | Lys | |
| | | | | 85 | | | | | 90 | | | | | 95 | | |

| | | | | | | | | | | | | | | | | |
|---|---|---|---|---|---|---|---|---|---|---|---|---|---|---|---|---|
| ccu | aac | ggu | gga | gcc | agc | aca | uau | gac | cuc | ucc | gga | ggu | uuc | acu | gca | 336 |
| Pro | Asn | Gly | Gly | Ala | Ser | Thr | Tyr | Asp | Leu | Ser | Gly | Gly | Phe | Thr | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| gca | gcc | aau | ggg | aau | gga | cua | cag | ggc | aca | cuu | cag | caa | ucu | ggu | ccu | 384 |
| Ala | Ala | Asn | Gly | Asn | Gly | Leu | Gln | Gly | Thr | Leu | Gln | Gln | Ser | Gly | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| gga | ucg | cag | cca | gaa | cug | ggc | gca | gac | auc | aag | acu | cug | acc | auu | acc | 432 |
| Gly | Ser | Gln | Pro | Glu | Leu | Gly | Ala | Asp | Ile | Lys | Thr | Leu | Thr | Ile | Thr | |
| | 130 | | | | | 135 | | | | | 140 | | | | | |

| | | | | | | | | | | | | | | | | |
|---|---|---|---|---|---|---|---|---|---|---|---|---|---|---|---|---|
| gug | gaa | aac | auc | acu | ccu | gac | aua | uug | cau | gca | aag | auu | ggc | gcg | cca | 480 |
| Val | Glu | Asn | Ile | Thr | Pro | Asp | Ile | Leu | His | Ala | Lys | Ile | Gly | Ala | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gga | cga | ugg | gaa | guc | ccc | aaa | agc | auc | uuc | cug | acu | cca | aau | guc | aca | 528 |
| Gly | Arg | Trp | Glu | Val | Pro | Lys | Ser | Ile | Phe | Leu | Thr | Pro | Asn | Val | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| gca | ucu | aac | ggu | ccg | gca | aac | uac | caa | uuc | aac | uac | agu | gug | ucg | ccc | 576 |
| Ala | Ser | Asn | Gly | Pro | Ala | Asn | Tyr | Gln | Phe | Asn | Tyr | Ser | Val | Ser | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| uuc | aca | uuu | gcu | gug | gcu | cgc | gca | aac | aac | aau | ggu | cag | gcg | cuc | uuc | 624 |
| Phe | Thr | Phe | Ala | Val | Ala | Arg | Ala | Asn | Asn | Asn | Gly | Gln | Ala | Leu | Phe | |
| | | 195 | | | | | 200 | | | | | 205 | | | | |

| | | | | | | | | | | | | | | | | |
|---|---|---|---|---|---|---|---|---|---|---|---|---|---|---|---|---|
| aac | acu | guu | ggc | ucu | cgu | cug | guc | aug | aag | gac | caa | uac | aug | gaa | auc | 672 |
| Asn | Thr | Val | Gly | Ser | Arg | Leu | Val | Met | Lys | Asp | Gln | Tyr | Met | Glu | Ile | |
| | 210 | | | | | 215 | | | | | 220 | | | | | |

| | |
|---|---|
| ucc acc uca gug cca gag acu gcu gcu cug uau ggc cuu ggc gag cgc<br>Ser Thr Ser Val Pro Glu Thr Ala Ala Leu Tyr Gly Leu Gly Glu Arg<br>225                     230                             235                          240 | 720 |
| aca ucc ucc acu ggu aua gag cug cgu aga gau ggc auu ccu cuu gca<br>Thr Ser Ser Thr Gly Ile Glu Leu Arg Arg Asp Gly Ile Pro Leu Ala<br>                       245                             250                         255 | 768 |
| cuc ugg aac cgc gau cac cag gcg gcc uug ccu gau cag aau guc uau<br>Leu Trp Asn Arg Asp His Gln Ala Ala Leu Pro Asp Gln Asn Val Tyr<br>                   260                           265                         270 | 816 |
| ggc ucu cac ccu auc cug aug gau guc cgc gaa gau ggc aca gcg cau<br>Gly Ser His Pro Ile Leu Met Asp Val Arg Glu Asp Gly Thr Ala His<br>         275                            280                         285 | 864 |
| ggu gug cug cug cug aac agc aau ggc aug gau gug gug cug aca aag<br>Gly Val Leu Leu Leu Asn Ser Asn Gly Met Asp Val Val Leu Thr Lys<br>         290                            295                         300 | 912 |
| aca cga gug cag ugg agg guc cuu ggu ggu gug uuu gac uuc uac uuc<br>Thr Arg Val Gln Trp Arg Val Leu Gly Gly Val Phe Asp Phe Tyr Phe<br>305                     310                             315                          320 | 960 |
| uug aug ggu ccg acc cca aau gcu guc cug gau cag cug acc acc auc<br>Leu Met Gly Pro Thr Pro Asn Ala Val Leu Asp Gln Leu Thr Thr Ile<br>                   325                           330                         335 | 1008 |
| auc ggc cgc ccu guc aug ccu cca uac ugg agu uug ggc cug aug aac<br>Ile Gly Arg Pro Val Met Pro Pro Tyr Trp Ser Leu Gly Leu Met Asn<br>                   340                           345                         350 | 1056 |
| agc aaa uau ggu uau gga ucu gcu gag uuc uac gau cag auc cuu aau<br>Ser Lys Tyr Gly Tyr Gly Ser Ala Glu Phe Tyr Asp Gln Ile Leu Asn<br>         355                            360                         365 | 1104 |
| ggc uau ggg aau gcc agc auu ccc uug gaa aca uuu gug uca gac uca<br>Gly Tyr Gly Asn Ala Ser Ile Pro Leu Glu Thr Phe Val Ser Asp Ser<br>         370                            375                         380 | 1152 |
| cag uac aug gac cac gau cag gac uuc acg cuu ggc agc aca uuc ucu<br>Gln Tyr Met Asp His Asp Gln Asp Phe Thr Leu Gly Ser Thr Phe Ser<br>385                     390                             395                          400 | 1200 |
| cuu ccu gau aug aag aau uuc cug aac aga auc aga gcc caa ggg cag<br>Leu Pro Asp Met Lys Asn Phe Leu Asn Arg Ile Arg Ala Gln Gly Gln<br>                   405                           410                         415 | 1248 |
| cga ugg guu cca auc cug gac cca aau auu cac auc aaa aag ggg uau<br>Arg Trp Val Pro Ile Leu Asp Pro Asn Ile His Ile Lys Lys Gly Tyr<br>                   420                           425                         430 | 1296 |
| gcg ccu uac gac agc ggc auc aag gca gau auc uuc auc aaa gau guu<br>Ala Pro Tyr Asp Ser Gly Ile Lys Ala Asp Ile Phe Ile Lys Asp Val<br>         435                            440                         445 | 1344 |
| uca ggg agc ccg uau guu ggc cag cuu ugg ccu ggu gca ugc cau ugg<br>Ser Gly Ser Pro Tyr Val Gly Gln Leu Trp Pro Gly Ala Cys His Trp<br>         450                            455                         460 | 1392 |
| ccu gac uuc aag aac ccc aau gca acu acu ugg ugg acc agc cag auu<br>Pro Asp Phe Lys Asn Pro Asn Ala Thr Thr Trp Trp Thr Ser Gln Ile<br>465                     470                             475                          480 | 1440 |
| aag agc guc uac gau gac uug gag aug gau ggc auc ugg auu gac aug<br>Lys Ser Val Tyr Asp Asp Leu Glu Met Asp Gly Ile Trp Ile Asp Met<br>                   485                           490                         495 | 1488 |
| aac gag ccc uca aau uac ugc acc gga gau guc ugc ugg aau gau gac<br>Asn Glu Pro Ser Asn Tyr Cys Thr Gly Asp Val Cys Trp Asn Asp Asp<br>         500                            505                         510 | 1536 |
| acu gug cca gcg cgc aau gau uuc gug ugc aug cuc ggc ugc guc agc<br>Thr Val Pro Ala Arg Asn Asp Phe Val Cys Met Leu Gly Cys Val Ser<br>         515                            520                         525 | 1584 |
| ggc aag gac cag gug aug gcc aca acc ggc aac aag agc auc acu cuc<br>Gly Lys Asp Gln Val Met Ala Thr Thr Gly Asn Lys Ser Ile Thr Leu | 1632 |

-continued

| | | | | | | | | | | | | | | | | |
|---|---|---|---|---|---|---|---|---|---|---|---|---|---|---|---|---|
| | 530 | | | | | 535 | | | | | 540 | | | | | |
| aac | gaa | agc | uac | uuu | aac | ccg | cca | uac | acc | auu | aac | aac | ggc | gac | aac | 1680 |
| Asn | Glu | Ser | Tyr | Phe | Asn | Pro | Pro | Tyr | Thr | Ile | Asn | Asn | Gly | Asp | Asn | |
| 545 | | | | 550 | | | | | 555 | | | | | 560 | | |
| gcc | uac | aac | auc | agc | uac | aag | aca | gug | gca | gua | acg | gca | uac | cac | uau | 1728 |
| Ala | Tyr | Asn | Ile | Ser | Tyr | Lys | Thr | Val | Ala | Val | Thr | Ala | Tyr | His | Tyr | |
| | | | | | 565 | | | | | 570 | | | | | 575 | |
| gac | ggc | acc | uug | gug | uac | aac | gcg | cac | aac | cug | uau | ggc | aug | cug | gag | 1776 |
| Asp | Gly | Thr | Leu | Val | Tyr | Asn | Ala | His | Asn | Leu | Tyr | Gly | Met | Leu | Glu | |
| | | | 580 | | | | | 585 | | | | | 590 | | | |
| acg | cug | gcc | aca | acu | ucu | gcu | cug | cag | aag | cug | cgc | aac | aag | cgc | caa | 1824 |
| Thr | Leu | Ala | Thr | Thr | Ser | Ala | Leu | Gln | Lys | Leu | Arg | Asn | Lys | Arg | Gln | |
| | | 595 | | | | | 600 | | | | | 605 | | | | |
| uuc | auc | cua | acc | agg | ucc | acu | uuc | cug | ggc | ucu | gga | gcc | uau | gca | gcc | 1872 |
| Phe | Ile | Leu | Thr | Arg | Ser | Thr | Phe | Leu | Gly | Ser | Gly | Ala | Tyr | Ala | Ala | |
| | 610 | | | | | 615 | | | | | 620 | | | | | |
| cau | ugg | acc | ggu | gac | acc | aau | gcc | aag | ugg | gag | gac | aug | cga | ugg | uca | 1920 |
| His | Trp | Thr | Gly | Asp | Thr | Asn | Ala | Lys | Trp | Glu | Asp | Met | Arg | Trp | Ser | |
| 625 | | | | 630 | | | | | 635 | | | | | 640 | | |
| auc | aca | acc | guc | cug | aau | aau | ggc | auu | gcc | ggc | auc | ucc | uuc | ucu | gga | 1968 |
| Ile | Thr | Thr | Val | Leu | Asn | Asn | Gly | Ile | Ala | Gly | Ile | Ser | Phe | Ser | Gly | |
| | | | | | 645 | | | | | 650 | | | | | 655 | |
| gca | gac | auc | ugc | ggg | uuc | aug | aug | cau | gcc | acu | gau | gag | cug | ugc | uca | 2016 |
| Ala | Asp | Ile | Cys | Gly | Phe | Met | Met | His | Ala | Thr | Asp | Glu | Leu | Cys | Ser | |
| | | | 660 | | | | | 665 | | | | | 670 | | | |
| cgc | ugg | gca | gcu | guu | ggu | gcc | uuc | uac | ccu | uac | gcc | cgc | aac | cac | cau | 2064 |
| Arg | Trp | Ala | Ala | Val | Gly | Ala | Phe | Tyr | Pro | Tyr | Ala | Arg | Asn | His | His | |
| | | 675 | | | | | 680 | | | | | 685 | | | | |
| ucc | gau | ggc | ugg | cag | gag | uuc | uuc | agg | ugg | gag | ucc | acg | uca | aua | gcu | 2112 |
| Ser | Asp | Gly | Trp | Gln | Glu | Phe | Phe | Arg | Trp | Glu | Ser | Thr | Ser | Ile | Ala | |
| | 690 | | | | | 695 | | | | | 700 | | | | | |
| gca | agg | aag | gug | uuc | acg | acg | cgc | uac | agg | cug | cug | ccc | uac | cug | uac | 2160 |
| Ala | Arg | Lys | Val | Phe | Thr | Thr | Arg | Tyr | Arg | Leu | Leu | Pro | Tyr | Leu | Tyr | |
| 705 | | | | 710 | | | | | 715 | | | | | 720 | | |
| acc | gcu | uuc | uuu | gac | ucg | cac | acc | uau | ggg | ugc | ccu | guu | gcg | cgg | cca | 2208 |
| Thr | Ala | Phe | Phe | Asp | Ser | His | Thr | Tyr | Gly | Cys | Pro | Val | Ala | Arg | Pro | |
| | | | | | 725 | | | | | 730 | | | | | 735 | |
| cug | uuc | uuc | acc | uuc | ccg | gcg | gac | aac | acc | acg | cgc | agc | auc | uca | gag | 2256 |
| Leu | Phe | Phe | Thr | Phe | Pro | Ala | Asp | Asn | Thr | Thr | Arg | Ser | Ile | Ser | Glu | |
| | | | 740 | | | | | 745 | | | | | 750 | | | |
| cag | ugg | aug | aug | ggc | gau | gcu | cug | cug | gug | ucu | ccu | auc | cuc | uau | gag | 2304 |
| Gln | Trp | Met | Met | Gly | Asp | Ala | Leu | Leu | Val | Ser | Pro | Ile | Leu | Tyr | Glu | |
| | | 755 | | | | | 760 | | | | | 765 | | | | |
| aag | acc | acc | aca | gua | aag | gca | uac | uuc | ccc | aag | gga | acc | ugg | uau | gac | 2352 |
| Lys | Thr | Thr | Thr | Val | Lys | Ala | Tyr | Phe | Pro | Lys | Gly | Thr | Trp | Tyr | Asp | |
| | 770 | | | | | 775 | | | | | 780 | | | | | |
| uuu | uac | acc | ggc | aga | guu | guc | gau | gcc | ucc | gcu | ggc | aag | uau | gac | | 2400 |
| Phe | Tyr | Thr | Gly | Arg | Val | Val | Asp | Ala | Ser | Ala | Gly | Lys | Tyr | Asp | | |
| 785 | | | | 790 | | | | | 795 | | | | | 800 | | |
| agu | guc | ucg | gcu | gac | auc | acu | gac | aau | gug | ccg | cug | cau | guc | cuu | ggc | 2448 |
| Ser | Val | Ser | Ala | Asp | Ile | Thr | Asp | Asn | Val | Pro | Leu | His | Val | Leu | Gly | |
| | | | | | 805 | | | | | 810 | | | | | 815 | |
| ggc | aac | auc | auu | ccc | aua | gcu | cug | ggc | uca | caa | uuc | aug | cuc | acc | caa | 2496 |
| Gly | Asn | Ile | Ile | Pro | Ile | Ala | Leu | Gly | Ser | Gln | Phe | Met | Leu | Thr | Gln | |
| | | | 820 | | | | | 825 | | | | | 830 | | | |
| gcu | guu | cgc | aac | gcc | agc | cau | gcc | cuu | guu | guu | gcc | uuc | ccc | aag | gcc | 2544 |
| Ala | Val | Arg | Asn | Ala | Ser | His | Ala | Leu | Val | Val | Ala | Phe | Pro | Lys | Ala | |
| | | 835 | | | | | 840 | | | | | 845 | | | | |
| aac | ucc | acu | uau | gca | ggc | gac | cgg | ugc | ggu | ggc | cga | ugu | ggc | gga | gcu | 2592 |

```
Asn Ser Thr Tyr Ala Gly Asp Arg Cys Gly Arg Cys Gly Gly Ala
            850                 855                 860 cca cag gcu gga gug cug aau gcc ugu ggc cac aug uac cuu gac cag      2640
Pro Gln Ala Gly Val Leu Asn Ala Cys Gly His Met Tyr Leu Asp Gln
865                 870                 875                 880 ggc gag gag cug aac cug uca cgg aac cuc aac aac uac cuu aac cug      2688
Gly Glu Glu Leu Asn Leu Ser Arg Asn Leu Asn Asn Tyr Leu Asn Leu
                885                 890                 895 gca uca cag aug gug cag cag gcg agc ggu ucc uac aag ggu uuc cug      2736
Ala Ser Gln Met Val Gln Gln Ala Ser Gly Ser Tyr Lys Gly Phe Leu
                900                 905                 910 agu gca acc uuc gcc ggc acu ccu ggc ggc uca ucu ggc gcc acc ugc      2784
Ser Ala Thr Phe Ala Gly Thr Pro Gly Gly Ser Ser Gly Ala Thr Cys
                915                 920                 925 gga aag gau gac agc ugg ucg ugg ccg guc auu gac acu guc auu guc      2832
Gly Lys Asp Asp Ser Trp Ser Trp Pro Val Ile Asp Thr Val Ile Val
                930                 935                 940 aug ggc acu ggu ccu gua gau ggc gau ucu auu guu guu cag gcu gug      2880
Met Gly Thr Gly Pro Val Asp Gly Asp Ser Ile Val Val Gln Ala Val
945                 950                 955                 960 uca gca ucg agc aca acu ccu gga aca gug cag aca gcg ucu gug gac      2928
Ser Ala Ser Ser Thr Thr Pro Gly Thr Val Gln Thr Ala Ser Val Asp
                965                 970                 975 agc acu cca ggc guc aca aac cuc uca acg ggc acc gcc aag uau gac      2976
Ser Thr Pro Gly Val Thr Asn Leu Ser Thr Gly Thr Ala Lys Tyr Asp
                980                 985                 990 gcc acg cug cag aag cuc acc auc ucc ggc cug aac uuc cag cug acg      3024
Ala Thr Leu Gln Lys Leu Thr Ile Ser Gly Leu Asn Phe Gln Leu Thr
                995                 1000                1005 ugc ccc acg ggu cug cgc auc agc ugg agc gcu gga gcc ccu uca         3069
Cys Pro Thr Gly Leu Arg Ile Ser Trp Ser Ala Gly Ala Pro Ser
        1010                1015                1020 gcg ccu gcc agc aca cca gca gcc gcg acc acg gcc gcg gca guc         3114
Ala Pro Ala Ser Thr Pro Ala Ala Ala Thr Thr Ala Ala Ala Val
        1025                1030                1035 uuc ggc acg ccu guc aag gac ccu ccc ucg ccg ccc aac agu gug         3159
Phe Gly Thr Pro Val Lys Asp Pro Pro Ser Pro Pro Asn Ser Val
        1040                1045                1050 guc ucg ccc ccg ggg ggu gga ucg agc ccg acc ucc aau uuc ggg         3204
Val Ser Pro Pro Gly Gly Gly Ser Ser Pro Thr Ser Asn Phe Gly
        1055                1060                1065 ucg ccc agc agc ccc ucu ucc ggc agu ucc ccg uca cag ucg ucg         3249
Ser Pro Ser Ser Pro Ser Ser Gly Ser Ser Pro Ser Gln Ser Ser
        1070                1075                1080 ucc gcu gcg ucu ccc agu ggc agc agc ucu uca ggg ucg ccg ucu         3294
Ser Ala Ala Ser Pro Ser Gly Ser Ser Ser Ser Gly Ser Pro Ser
        1085                1090                1095 ucu agc agu ggc ucu gga ucc ucc agu ggc ucu ggg ucu ccc agc         3339
Ser Ser Ser Gly Ser Gly Ser Ser Ser Gly Ser Gly Ser Pro Ser
        1100                1105                1110 ggc uca ccc uac agc ucg agu ggc agc ucu ggc ucg cca gcu guc         3384
Gly Ser Pro Tyr Ser Ser Ser Gly Ser Ser Gly Ser Pro Ala Val
        1115                1120                1125 ucc agc agc ccc uca ggc ucc ggc aca ccg ucg ucu ggc agc             3429
Ser Ser Ser Pro Ser Gly Ser Gly Thr Pro Ser Ser Gly Ser
        1130                1135                1140 ccc uca ucc uac agc agc uac agc agc ccc uca ggc uac ggc agc         3474
Pro Ser Ser Tyr Ser Ser Tyr Ser Ser Pro Ser Gly Tyr Gly Ser
        1145                1150                1155
```

-continued

| | | | | | | | | | | | | |
|---|---|---|---|---|---|---|---|---|---|---|---|---|
| ucu | uca | ccu | ucu | uac | agc | agc | ccc | ucg | uca | uac | agc | ccc ucc uca |
| Ser | Ser | Pro | Ser | Tyr | Ser | Ser | Pro | Ser | Ser | Tyr | Ser | Pro Ser Ser |
| 1160 | | | | 1165 | | | | | 1170 | | | |

3519

| | | | | | | | | | | | | |
|---|---|---|---|---|---|---|---|---|---|---|---|---|
| uac | agc | agc | ucu | ucg | uac | agc | ccc | ucu | ucg | uac | agc | agc ucg cca |
| Tyr | Ser | Ser | Ser | Ser | Tyr | Ser | Pro | Ser | Ser | Tyr | Ser | Ser Ser Pro |
| 1175 | | | | 1180 | | | | | 1185 | | | |

3564

| | | | | | | | | | | | | |
|---|---|---|---|---|---|---|---|---|---|---|---|---|
| ucc | agc | uac | agc | agc | agu | agc | agu | cgc | agc | ccc | agc | ccg acc uca |
| Ser | Ser | Tyr | Ser | Ser | Ser | Ser | Ser | Arg | Ser | Pro | Ser | Pro Thr Ser |
| 1190 | | | | 1195 | | | | | 1200 | | | |

3609

| | | | | | | | | | | | | |
|---|---|---|---|---|---|---|---|---|---|---|---|---|
| ucc | uac | uac | agc | ccc | agc | agg | agc | ucu | uca | gga | ggc | ggu gga ggu |
| Ser | Tyr | Tyr | Ser | Pro | Ser | Arg | Ser | Ser | Ser | Gly | Gly | Gly Gly Gly |
| 1205 | | | | 1210 | | | | | 1215 | | | |

3654

| | | | | | | | | | | | | |
|---|---|---|---|---|---|---|---|---|---|---|---|---|
| ggc | ccu | ggg | ggc | ggu | ggc | ccu | gga | ggu | ggc | ggc | ccu | gga ggc ggu |
| Gly | Pro | Gly | Gly | Gly | Gly | Pro | Gly | Gly | Gly | Gly | Pro | Gly Gly Gly |
| 1220 | | | | 1225 | | | | | 1230 | | | |

3699

| | | | |
|---|---|---|---|
| ccc | uuc | uuu | gga uga |
| Pro | Phe | Phe | Gly |
| 1235 | | | |

3714

<210> SEQ ID NO 3
<211> LENGTH: 1237
<212> TYPE: PRT
<213> ORGANISM: Pseudococcomyxa sp.

<400> SEQUENCE: 3

Met Ala Asn Glu Ala Arg Arg Leu Gly Arg Leu Ser Ala Ser Ser Ala
1               5                   10                  15

Lys Leu Cys Leu Leu Val Val Ala Leu Ser Ser Ala Leu Val Arg Cys
            20                  25                  30

Gln Ser Pro Gly Gly Phe Gly Ser Pro Pro Gly Gln Gly Gln Cys
        35                  40                  45

Asp Ala Ser Gly Pro Arg Val Glu Cys Gly Trp Asn Gly Ile Glu Ser
    50                  55                  60

Trp Lys Cys Ala Ser Lys Gly Cys Cys Tyr Asp Pro Asn Thr Pro Thr
65                  70                  75                  80

Gln Val Gly Thr Ala Ser Val Lys Val Thr Thr Pro Val Cys Phe Lys
                85                  90                  95

Pro Asn Gly Gly Ala Ser Thr Tyr Asp Leu Ser Gly Gly Phe Thr Ala
            100                 105                 110

Ala Ala Asn Gly Asn Gly Leu Gln Gly Thr Leu Gln Gln Ser Gly Pro
        115                 120                 125

Gly Ser Gln Pro Glu Leu Gly Ala Asp Ile Lys Thr Leu Thr Ile Thr
    130                 135                 140

Val Glu Asn Ile Thr Pro Asp Ile Leu His Ala Lys Ile Gly Ala Pro
145                 150                 155                 160

Gly Arg Trp Glu Val Pro Lys Ser Ile Phe Leu Thr Pro Asn Val Thr
                165                 170                 175

Ala Ser Asn Gly Pro Ala Asn Tyr Gln Phe Asn Tyr Ser Val Ser Pro
            180                 185                 190

Phe Thr Phe Ala Val Ala Arg Ala Asn Asn Asn Gly Gln Ala Leu Phe
        195                 200                 205

Asn Thr Val Gly Ser Arg Leu Val Met Lys Asp Gln Tyr Met Glu Ile
    210                 215                 220

Ser Thr Ser Val Pro Glu Thr Ala Ala Leu Tyr Gly Leu Gly Glu Arg
225                 230                 235                 240

Thr Ser Ser Thr Gly Ile Glu Leu Arg Arg Asp Gly Ile Pro Leu Ala
                245                 250                 255

```
Leu Trp Asn Arg Asp His Gln Ala Ala Leu Pro Asp Gln Asn Val Tyr
            260                 265                 270

Gly Ser His Pro Ile Leu Met Asp Val Arg Glu Asp Gly Thr Ala His
            275                 280                 285

Gly Val Leu Leu Leu Asn Ser Asn Gly Met Asp Val Val Leu Thr Lys
            290                 295                 300

Thr Arg Val Gln Trp Arg Val Leu Gly Val Phe Asp Phe Tyr Phe
305                 310                 315                 320

Leu Met Gly Pro Thr Pro Asn Ala Val Leu Asp Gln Leu Thr Thr Ile
            325                 330                 335

Ile Gly Arg Pro Val Met Pro Pro Tyr Trp Ser Leu Gly Leu Met Asn
            340                 345                 350

Ser Lys Tyr Gly Tyr Gly Ser Ala Glu Phe Tyr Asp Gln Ile Leu Asn
            355                 360                 365

Gly Tyr Gly Asn Ala Ser Ile Pro Leu Glu Thr Phe Val Ser Asp Ser
            370                 375                 380

Gln Tyr Met Asp His Asp Gln Asp Phe Thr Leu Gly Ser Thr Phe Ser
385                 390                 395                 400

Leu Pro Asp Met Lys Asn Phe Leu Asn Arg Ile Arg Ala Gln Gly Gln
            405                 410                 415

Arg Trp Val Pro Ile Leu Asp Pro Asn Ile His Ile Lys Lys Gly Tyr
            420                 425                 430

Ala Pro Tyr Asp Ser Gly Ile Lys Ala Asp Ile Phe Ile Lys Asp Val
            435                 440                 445

Ser Gly Ser Pro Tyr Val Gly Gln Leu Trp Pro Gly Ala Cys His Trp
            450                 455                 460

Pro Asp Phe Lys Asn Pro Asn Ala Thr Thr Trp Trp Thr Ser Gln Ile
465                 470                 475                 480

Lys Ser Val Tyr Asp Asp Leu Glu Met Asp Gly Ile Trp Ile Asp Met
            485                 490                 495

Asn Glu Pro Ser Asn Tyr Cys Thr Gly Asp Val Cys Trp Asn Asp Asp
            500                 505                 510

Thr Val Pro Ala Arg Asn Asp Phe Val Cys Met Leu Gly Cys Val Ser
            515                 520                 525

Gly Lys Asp Gln Val Met Ala Thr Thr Gly Asn Lys Ser Ile Thr Leu
            530                 535                 540

Asn Glu Ser Tyr Phe Asn Pro Pro Tyr Thr Ile Asn Asn Gly Asp Asn
545                 550                 555                 560

Ala Tyr Asn Ile Ser Tyr Lys Thr Val Ala Val Thr Ala Tyr His Tyr
            565                 570                 575

Asp Gly Thr Leu Val Tyr Asn Ala His Asn Leu Tyr Gly Met Leu Glu
            580                 585                 590

Thr Leu Ala Thr Thr Ser Ala Leu Gln Lys Leu Arg Asn Lys Arg Gln
            595                 600                 605

Phe Ile Leu Thr Arg Ser Thr Phe Leu Gly Ser Gly Ala Tyr Ala Ala
            610                 615                 620

His Trp Thr Gly Asp Thr Asn Ala Lys Trp Glu Asp Met Arg Trp Ser
625                 630                 635                 640

Ile Thr Thr Val Leu Asn Asn Gly Ile Ala Gly Ile Ser Phe Ser Gly
            645                 650                 655

Ala Asp Ile Cys Gly Phe Met Met His Ala Thr Asp Glu Leu Cys Ser
            660                 665                 670
```

-continued

```
Arg Trp Ala Ala Val Gly Ala Phe Tyr Pro Tyr Ala Arg Asn His His
675                 680                 685

Ser Asp Gly Trp Gln Glu Phe Phe Arg Trp Glu Ser Thr Ser Ile Ala
690                 695                 700

Ala Arg Lys Val Phe Thr Thr Arg Tyr Arg Leu Leu Pro Tyr Leu Tyr
705                 710                 715                 720

Thr Ala Phe Phe Asp Ser His Thr Tyr Gly Cys Pro Val Ala Arg Pro
                725                 730                 735

Leu Phe Phe Thr Phe Pro Ala Asp Asn Thr Thr Arg Ser Ile Ser Glu
                740                 745                 750

Gln Trp Met Met Gly Asp Ala Leu Leu Val Ser Pro Ile Leu Tyr Glu
                755                 760                 765

Lys Thr Thr Thr Val Lys Ala Tyr Phe Pro Lys Gly Thr Trp Tyr Asp
770                 775                 780

Phe Tyr Thr Gly Arg Val Val Asp Ala Ser Ala Gly Gly Lys Tyr Asp
785                 790                 795                 800

Ser Val Ser Ala Asp Ile Thr Asp Asn Val Pro Leu His Val Leu Gly
                805                 810                 815

Gly Asn Ile Ile Pro Ile Ala Leu Gly Ser Gln Phe Met Leu Thr Gln
                820                 825                 830

Ala Val Arg Asn Ala Ser His Ala Leu Val Val Ala Phe Pro Lys Ala
                835                 840                 845

Asn Ser Thr Tyr Ala Gly Asp Arg Cys Gly Gly Arg Cys Gly Gly Ala
                850                 855                 860

Pro Gln Ala Gly Val Leu Asn Ala Cys Gly His Met Tyr Leu Asp Gln
865                 870                 875                 880

Gly Glu Glu Leu Asn Leu Ser Arg Asn Leu Asn Asn Tyr Leu Asn Leu
                885                 890                 895

Ala Ser Gln Met Val Gln Ala Ser Gly Ser Tyr Lys Gly Phe Leu
                900                 905                 910

Ser Ala Thr Phe Ala Gly Thr Pro Gly Gly Ser Gly Ala Thr Cys
                915                 920                 925

Gly Lys Asp Asp Ser Trp Ser Trp Pro Val Ile Asp Thr Val Ile Val
930                 935                 940

Met Gly Thr Gly Pro Val Asp Gly Asp Ser Ile Val Val Gln Ala Val
945                 950                 955                 960

Ser Ala Ser Ser Thr Thr Pro Gly Thr Val Gln Thr Ala Ser Val Asp
                965                 970                 975

Ser Thr Pro Gly Val Thr Asn Leu Ser Thr Gly Thr Ala Lys Tyr Asp
                980                 985                 990

Ala Thr Leu Gln Lys Leu Thr Ile Ser Gly Leu Asn Phe Gln Leu Thr
                995                 1000                1005

Cys Pro Thr Gly Leu Arg Ile Ser Trp Ser Ala Gly Ala Pro Ser
        1010            1015                1020

Ala Pro Ala Ser Thr Pro Ala Ala Ala Thr Ala Ala Ala Val
        1025            1030                1035

Phe Gly Thr Pro Val Lys Asp Pro Pro Ser Pro Asn Ser Val
        1040            1045                1050

Val Ser Pro Pro Gly Gly Gly Ser Ser Pro Thr Ser Asn Phe Gly
        1055            1060                1065

Ser Pro Ser Ser Pro Ser Gly Ser Ser Pro Ser Gln Ser Ser
        1070            1075                1080

Ser Ala Ala Ser Pro Ser Gly Ser Ser Ser Ser Gly Ser Pro Ser
```

```
                1085                1090                1095
Ser  Ser  Ser  Gly  Ser  Gly  Ser  Ser  Gly  Ser  Gly  Ser  Pro  Ser
     1100                1105                1110

Gly  Ser  Pro  Tyr  Ser  Ser  Ser  Gly  Ser  Ser  Gly  Ser  Pro  Ala  Val
     1115                1120                1125

Ser  Ser  Ser  Pro  Ser  Gly  Ser  Gly  Thr  Pro  Ser  Ser  Ser  Gly  Ser
     1130                1135                1140

Pro  Ser  Ser  Tyr  Ser  Ser  Tyr  Ser  Ser  Pro  Ser  Gly  Tyr  Gly  Ser
     1145                1150                1155

Ser  Ser  Pro  Ser  Tyr  Ser  Ser  Pro  Ser  Ser  Tyr  Ser  Pro  Ser  Ser
     1160                1165                1170

Tyr  Ser  Ser  Ser  Tyr  Ser  Pro  Ser  Ser  Tyr  Ser  Ser  Ser  Pro
     1175                1180                1185

Ser  Ser  Tyr  Ser  Ser  Ser  Ser  Arg  Ser  Pro  Ser  Pro  Thr  Ser
     1190                1195                1200

Ser  Tyr  Tyr  Ser  Pro  Ser  Arg  Ser  Ser  Ser  Gly  Gly  Gly  Gly  Gly
     1205                1210                1215

Gly  Pro  Gly  Gly  Gly  Gly  Pro  Gly  Gly  Gly  Gly  Pro  Gly  Gly  Gly
     1220                1225                1230

Pro  Phe  Phe  Gly
     1235

<210> SEQ ID NO 4
<211> LENGTH: 569
<212> TYPE: PRT
<213> ORGANISM: Pseudococcomyxa sp.

<400> SEQUENCE: 4

Leu  Val  Met  Lys  Asp  Gln  Tyr  Met  Glu  Ile  Ser  Thr  Ser  Val  Pro  Glu
1                 5                  10                 15

Thr  Ala  Ala  Leu  Tyr  Gly  Leu  Gly  Glu  Arg  Thr  Ser  Ser  Thr  Gly  Ile
             20                  25                  30

Glu  Leu  Arg  Arg  Asp  Gly  Ile  Pro  Leu  Ala  Leu  Trp  Asn  Arg  Asp  His
         35                  40                  45

Gln  Ala  Ala  Leu  Pro  Asp  Gln  Asn  Val  Tyr  Gly  Ser  His  Pro  Ile  Leu
     50                  55                  60

Met  Asp  Val  Arg  Glu  Asp  Gly  Thr  Ala  His  Gly  Val  Leu  Leu  Leu  Asn
65                  70                  75                  80

Ser  Asn  Gly  Met  Asp  Val  Val  Leu  Thr  Lys  Thr  Arg  Val  Gln  Trp  Arg
                 85                  90                  95

Val  Leu  Gly  Gly  Val  Phe  Asp  Phe  Tyr  Phe  Leu  Met  Gly  Pro  Thr  Pro
            100                 105                 110

Asn  Ala  Val  Leu  Asp  Gln  Leu  Thr  Thr  Ile  Ile  Gly  Arg  Pro  Val  Met
        115                 120                 125

Pro  Pro  Tyr  Trp  Ser  Leu  Gly  Leu  Met  Asn  Ser  Lys  Tyr  Gly  Tyr  Gly
    130                 135                 140

Ser  Ala  Glu  Phe  Tyr  Asp  Gln  Ile  Leu  Asn  Gly  Tyr  Gly  Asn  Ala  Ser
145                 150                 155                 160

Ile  Pro  Leu  Glu  Thr  Phe  Val  Ser  Asp  Ser  Gln  Tyr  Met  Asp  His  Asp
                165                 170                 175

Gln  Asp  Phe  Thr  Leu  Gly  Ser  Thr  Phe  Ser  Leu  Pro  Asp  Met  Lys  Asn
            180                 185                 190

Phe  Leu  Asn  Arg  Ile  Arg  Ala  Gln  Gly  Gln  Arg  Trp  Val  Pro  Ile  Leu
        195                 200                 205
```

Asp Pro Asn Ile His Ile Lys Lys Gly Tyr Ala Pro Tyr Asp Ser Gly
    210                 215                 220

Ile Lys Ala Asp Ile Phe Ile Lys Asp Val Ser Gly Ser Pro Tyr Val
225                 230                 235                 240

Gly Gln Leu Trp Pro Gly Ala Cys His Trp Pro Asp Phe Lys Asn Pro
                245                 250                 255

Asn Ala Thr Thr Trp Thr Ser Gln Ile Lys Ser Val Tyr Asp Asp
            260                 265                 270

Leu Glu Met Asp Gly Ile Trp Ile Asp Met Asn Glu Pro Ser Asn Tyr
            275                 280                 285

Cys Thr Gly Asp Val Cys Trp Asn Asp Thr Val Pro Ala Arg Asn
290                 295                 300

Asp Phe Val Cys Met Leu Gly Cys Val Ser Gly Lys Asp Gln Val Met
305                 310                 315                 320

Ala Thr Thr Gly Asn Lys Ser Ile Thr Leu Asn Glu Ser Tyr Phe Asn
                325                 330                 335

Pro Pro Tyr Thr Ile Asn Asn Gly Asp Asn Ala Tyr Asn Ile Ser Tyr
            340                 345                 350

Lys Thr Val Ala Val Thr Ala Tyr His Tyr Asp Gly Thr Leu Val Tyr
            355                 360                 365

Asn Ala His Asn Leu Tyr Gly Met Leu Glu Thr Leu Ala Thr Thr Ser
370                 375                 380

Ala Leu Gln Lys Leu Arg Asn Lys Arg Gln Phe Ile Leu Thr Arg Ser
385                 390                 395                 400

Thr Phe Leu Gly Ser Gly Ala Tyr Ala Ala His Trp Thr Gly Asp Thr
                405                 410                 415

Asn Ala Lys Trp Glu Asp Met Arg Trp Ser Ile Thr Thr Val Leu Asn
            420                 425                 430

Asn Gly Ile Ala Gly Ile Ser Phe Ser Gly Ala Asp Ile Cys Gly Phe
            435                 440                 445

Met Met His Ala Thr Asp Glu Leu Cys Ser Arg Trp Ala Ala Val Gly
            450                 455                 460

Ala Phe Tyr Pro Tyr Ala Arg Asn His His Ser Asp Gly Trp Gln Glu
465                 470                 475                 480

Phe Phe Arg Trp Glu Ser Thr Ser Ile Ala Ala Arg Lys Val Phe Thr
                485                 490                 495

Thr Arg Tyr Arg Leu Leu Pro Tyr Leu Tyr Thr Ala Phe Phe Asp Ser
            500                 505                 510

His Thr Tyr Gly Cys Pro Val Ala Arg Pro Leu Phe Phe Thr Phe Pro
            515                 520                 525

Ala Asp Asn Thr Thr Arg Ser Ile Ser Glu Gln Trp Met Met Gly Asp
530                 535                 540

Ala Leu Leu Val Ser Pro Ile Leu Tyr Glu Lys Thr Thr Val Lys
545                 550                 555                 560

Ala Tyr Phe Pro Lys Gly Thr Trp Tyr
                565

<210> SEQ ID NO 5
<211> LENGTH: 3596
<212> TYPE: DNA
<213> ORGANISM: Pseudococcomyxa sp.

<400> SEQUENCE: 5
caagttatat ttagtacccc ctgaaagcac gctgcatgca agcgggaggt cacgccgttc    60

```
tgccagcact ctagcaagcg tcgacacaag aaattccttc atgtccacct ggatttacac    120
caaattgttc agcacacagt gagctagctg aacttgtggt atctccatcc ttgtgctttt    180
tgcttgtcca acgttgcagt cgatcagata gctgtgttcc atgctattgg gtcgtttctc    240
ctagggctca agatattgca tcagcttttg ataagttgtt gtagacttgt tttcgagtgg    300
cccagcgaca tgccaatgtt cagttcaatg caaacactca atgcattgcc attgatgcct    360
atcagccccc acgcaaaggc agcggccagg cacaacttga aggacagaa caatcggact     420 cagcaccagg tctgcgggcc ttccatctgc cgcgcgtcgg ccgcggtatc agaggagaga    480
ataacaaatg caaagcgcg ccctatgact ctccaagccc ctcagcagcc ttgcgaagcg     540
gggcgactta ccgatgatgg cacagctttc ttggaagagc acaggatccg aggttatgaa    600
gttgggccag atcagaagac caccattgtc acgatcgcga atctgttgca ggtatgttgt    660
ctggaatatt ctgaacctgc taagtctatg tccttttggt tgaggcaaac tgcaaaagag    720
tgctgtacag gaagcatttc ccattcttat gtgcaatgct gcaagaacgt tctttaaaca    780
agcctgcgag attgttttg ctcaaacaaa tgtgtatgga agccacttct gtctgggtct     840
tcccttttgc tttgatctct gacaaaagag tccctgatag gtggctgcac attgcgaagt    900
cgcccgcgac gcgatctgca aagcttcctt acacaagcaa aatgtgacat aagtgtttca    960
tgctgccgca ggaagtcgca gggaaccatg ctgttgcgct atggggacgc acagatgcag   1020
gctatgccca gaccccctc atggtggagc ggcatctcat ctttgctgtg accaggatgc    1080
agatcaggat ggacagctac ccgaaatggt gggaacttca ccaccaagtt ccttctatcg   1140
gcatagtttt agaggggcag tgacaggcag atgtcatgcc taagtgaata ttttgttcat   1200 tctcttttg ggaacagtct gcaagaaatc tttcgtggat gcaggggtga cctggtgcag    1260
attgagacct ggtttcagga ggaggggcga gtctcggcgt ccgcaactg atcctcacc     1320 aaccagtcca ctggcgagga aattggtcgc gccaccaggt gaggcctgca gggccccttg   1380
tgtattggca aggtcctggc tcccttagga ccatcaaata aacatacatg gcgacatttg   1440
acacatgttg ccaaaggata tgagcaagtg cgcgccttga ttgcttctag cgcatcaggt   1500
cagcaacatt tcaaaatctg gtgcgagctg gatcttttgt catgctgtcc tccaacagcg   1560
tgtagaacgc atgtcatgtg agtggttgct gaggttgggg tgaatgcgcg cagcacatgg   1620
gtgatggtaa acacgctgac gaggcggctc tcgaagatgc ctgacgagat gcgcgccaag   1680
atggagtacc tggcaccca tccctccagg tatggatttt gttattgtac acaacgttct    1740
tcgacgttga cagttcttgt cccaccacct tcagattgat tgtttgtgtc tttggacgtt   1800
gcttgatgca tgtcaccacc cttgttgacc atctctttga ttaacttgat gtgcatgtta   1860
atgttgggct gtgtctgggt ctgtgacact caatgaactg ccttgtgttt tgcagggatg   1920
tgctcccggc agcagaggtc cgccaaaaga tcccagacct gaggaccct ccagaggtga    1980 gagttcatgg actcctactc tgtgcctagg caaatgtgat gttcgtattg cacactcact   2040
tcatggcatc acgcacgtcc ttactctcat tcttcattgc tctggcgcac ttcccccagt   2100
atgagaacag gggcatatta ctgcaaatct gacgtgcaga gcagtgttag ttctccctgc   2160
aagaagcttg tcgcaatgt ggtatcaaag aggctctcag gacatcattt aggctttctg    2220
acgaccttgc atgtgcactg tagattgagg gcccggtgca ggtggcgcgg cgcagcgaca   2280
tggacatgaa tggccacatc aacaatgtca cctacctcgg atgggccctt gagactgtcc   2340
ctccagacgt ctacctcaac tacagttttgc atgaggtgac caggcttctg ccacttccca   2400
tgcaggactt gccgccccat taattccagc gtggcctgtg ttttcaaagc ttcgagccgg   2460
```

-continued

```
gctggttcag aacttcgttg actgacagtg gcagcagaca ggcgtgcaag cattaggtgt     2520
caatgtccaa gagtgcggaa tcgcccatcg tgggttttag aagacacgtt cttattcgtc     2580
agcgcttgtg gcacttgcag gtggagattg atttcaagtc cgagtgcatg gctgggcaga     2640
cagtggagtc cattggcagc cgcatcaagg aggacacaaa tggaaccggc atactaaggt     2700
aagaacagca acatctctgg tgggcacccc aatctgatcc atcacactat ggtaggtggg     2760
atcactgttg ttcagcacat ggaaacacaa tgatgtttgc actaatcacc ttagagtgaa     2820
cattgtttga cagacagttg tgggtacatt gactgagctg cggttctgtg cgtataggt      2880 tcgtgcactt gctgaggcgc tgtgatgaca gcggctgcta tgagctggtg agggcgcgta     2940
ccacatggcg gccgcagtat ggcaagctgc agctccactg agcagcctgt aaccacagat     3000
ctggtgactg agtggcacca ggttggctgg agcgtcacca acatcccagc aacattagtc     3060 cacaccccc tgctcaaaga cgctgcacct tcggaaggag tgagcggttc gtgagctgcc     3120
aatcaacatg tgcggtggtg ccaggcgtgt gttcagcct gcttgggctg cacggaagct      3180
ggggcaatta tcgaagcaac cttcaatgtc agtctcaacg ggtgtggctg agaagcgcgc     3240
aacttcctcg ctccagacaa acttagatag gctctattcc agacggttgg gggcatacaa     3300
gtcaagagtg gctaagtgct cagtgcggaa cgcattgaaa actcagtctt agctcaggtg     3360
aggatggtaa accccttcca ccaggtatta tgtcaagaac tgcccagcag cttgatgtgc     3420
gagatcctgt ggaagtgcac acggccacat tctgcatatt ttgtagataa aggtgggatg     3480
gtcacatttg ccacggggtt gtcaaagtgt gctgtctcgt gcacggtttc ttggatgtga     3540
ggtggcaaaa ttggtgactt tcagtggcga gaagtcagta aatacttgtg gataac         3596
```

<210> SEQ ID NO 6
<211> LENGTH: 1083
<212> TYPE: RNA
<213> ORGANISM: Pseudococcomyxa sp.
<220> FEATURE:
<221> NAME/KEY: CDS
<222> LOCATION: (1)..(1083)

<400> SEQUENCE: 6

```
aug cca aug uuc agu uca aug caa aca cuc aau gca uug cca uug aug       48
Met Pro Met Phe Ser Ser Met Gln Thr Leu Asn Ala Leu Pro Leu Met
1               5                   10                  15 ccu auc agc ccc cac gca aag gca gcg gcc agg cac aac uug aaa gga      96
Pro Ile Ser Pro His Ala Lys Ala Ala Ala Arg His Asn Leu Lys Gly
            20                  25                  30 cag aac aau cgg acu cag cac cag guc ugc ggg ccu ucc auc ugc cgc     144
Gln Asn Asn Arg Thr Gln His Gln Val Cys Gly Pro Ser Ile Cys Arg
        35                  40                  45 gcg ucg gcc gcg gua uca gag gag aga aua aca aau ggc aaa gcg cgc     192
Ala Ser Ala Ala Val Ser Glu Glu Arg Ile Thr Asn Gly Lys Ala Arg
    50                  55                  60 ccu aug acu cuc caa gcc ccu cag cag ccu ugc gaa gcg ggg cga cuu     240
Pro Met Thr Leu Gln Ala Pro Gln Gln Pro Cys Glu Ala Gly Arg Leu
65                  70                  75                  80 acc gau gau ggc aca gcu uuc uug gaa gag cac agg auc cga ggu uau     288
Thr Asp Asp Gly Thr Ala Phe Leu Glu Glu His Arg Ile Arg Gly Tyr
                85                  90                  95 gaa guu ggg cca gau cag aag acc acc auu guc acg auc gcg aau cug     336
Glu Val Gly Pro Asp Gln Lys Thr Thr Ile Val Thr Ile Ala Asn Leu
            100                 105                 110 uug cag gaa guc gca ggg aac cau gcu guu gcg cua ugg gga cgc aca     384
```

```
                Leu Gln Glu Val Ala Gly Asn His Ala Val Ala Leu Trp Gly Arg Thr
                    115                 120                 125 gau gca ggc uau gcc aca gac ccc cuc aug gug gag cgg cau cuc auc          432
Asp Ala Gly Tyr Ala Thr Asp Pro Leu Met Val Glu Arg His Leu Ile
130                 135                 140 uuu gcu gug acc agg aug cag auc agg aug gac agc uac ccg aaa ugg          480
Phe Ala Val Thr Arg Met Gln Ile Arg Met Asp Ser Tyr Pro Lys Trp
145                 150                 155                 160 ggu gac cug gug cag auu gag acc ugg uuu cag gag gag ggg cga guc          528
Gly Asp Leu Val Gln Ile Glu Thr Trp Phe Gln Glu Glu Gly Arg Val
                165                 170                 175 ucg gcg ugc cgc aac ugg auc cuc acc aac cag ucc acu ggc gag gaa          576
Ser Ala Cys Arg Asn Trp Ile Leu Thr Asn Gln Ser Thr Gly Glu Glu
            180                 185                 190 auu ggu cgc gcc acc agc aca ugg gug aug gua aac acg cug acg agg          624
Ile Gly Arg Ala Thr Ser Thr Trp Val Met Val Asn Thr Leu Thr Arg
        195                 200                 205 cgg cuc ucg aag aug ccu gac gag aug cgc gcc aag aug gag uac cug          672
Arg Leu Ser Lys Met Pro Asp Glu Met Arg Ala Lys Met Glu Tyr Leu
    210                 215                 220 gca ccc cau ccc ucc agg gau gug cuc ccg gca gca gag guc cgc caa          720
Ala Pro His Pro Ser Arg Asp Val Leu Pro Ala Ala Glu Val Arg Gln
225                 230                 235                 240 aag auc cca gac cuu gag gac ccu cca gag auu gag ggc ccg gug cag          768
Lys Ile Pro Asp Leu Glu Asp Pro Pro Glu Ile Glu Gly Pro Val Gln
                245                 250                 255 gug gcg cgg cgc agc gac aug gac aug aau ggc cac auc aac aau guc          816
Val Ala Arg Arg Ser Asp Met Asp Met Asn Gly His Ile Asn Asn Val
            260                 265                 270 acc uac cuc gga ugg gcc cuu gag acu guc ccu cca gac guc uac cuc          864
Thr Tyr Leu Gly Trp Ala Leu Glu Thr Val Pro Pro Asp Val Tyr Leu
        275                 280                 285 aac uac agu uug cau gag gug gag auu gau uuc aag ucc gag ugc aug          912
Asn Tyr Ser Leu His Glu Val Glu Ile Asp Phe Lys Ser Glu Cys Met
    290                 295                 300 gcu ggg cag aca gug gag ucc auu ggc agc cgc auc aag gag gac aca          960
Ala Gly Gln Thr Val Glu Ser Ile Gly Ser Arg Ile Lys Glu Asp Thr
305                 310                 315                 320 aau gga acc ggc aua cua agg uuc gug cac uug cug agg cgc ugu gau         1008
Asn Gly Thr Gly Ile Leu Arg Phe Val His Leu Leu Arg Arg Cys Asp
                325                 330                 335 gac agc ggc ugc uau gag cug gug agg gcg cgu acc aca ugg cgg ccg         1056
Asp Ser Gly Cys Tyr Glu Leu Val Arg Ala Arg Thr Thr Trp Arg Pro
            340                 345                 350 cag uau ggc aag cug cag cuc cac uga                                     1083
Gln Tyr Gly Lys Leu Gln Leu His
        355                 360

<210> SEQ ID NO 7
<211> LENGTH: 360
<212> TYPE: PRT
<213> ORGANISM: Pseudococcomyxa sp.

<400> SEQUENCE: 7

Met Pro Met Phe Ser Ser Met Gln Thr Leu Asn Ala Leu Pro Leu Met
1               5                   10                  15

Pro Ile Ser Pro His Ala Lys Ala Ala Ala Arg His Asn Leu Lys Gly
                20                  25                  30

Gln Asn Asn Arg Thr Gln His Gln Val Cys Gly Pro Ser Ile Cys Arg
            35                  40                  45
```

Ala Ser Ala Ala Val Ser Glu Glu Arg Ile Thr Asn Gly Lys Ala Arg
    50                  55                  60

Pro Met Thr Leu Gln Ala Pro Gln Gln Pro Cys Glu Ala Gly Arg Leu
65                  70                  75                  80

Thr Asp Asp Gly Thr Ala Phe Leu Glu Glu His Arg Ile Arg Gly Tyr
                85                  90                  95

Glu Val Gly Pro Asp Gln Lys Thr Thr Ile Val Thr Ile Ala Asn Leu
            100                 105                 110

Leu Gln Glu Val Ala Gly Asn His Ala Val Ala Leu Trp Gly Arg Thr
        115                 120                 125

Asp Ala Gly Tyr Ala Thr Asp Pro Leu Met Val Glu Arg His Leu Ile
    130                 135                 140

Phe Ala Val Thr Arg Met Gln Ile Arg Met Asp Ser Tyr Pro Lys Trp
145                 150                 155                 160

Gly Asp Leu Val Gln Ile Glu Thr Trp Phe Gln Glu Glu Gly Arg Val
                165                 170                 175

Ser Ala Cys Arg Asn Trp Ile Leu Thr Asn Gln Ser Thr Gly Glu Glu
            180                 185                 190

Ile Gly Arg Ala Thr Ser Thr Trp Val Met Val Asn Thr Leu Thr Arg
        195                 200                 205

Arg Leu Ser Lys Met Pro Asp Glu Met Arg Ala Lys Met Glu Tyr Leu
    210                 215                 220

Ala Pro His Pro Ser Arg Asp Val Leu Pro Ala Ala Glu Val Arg Gln
225                 230                 235                 240

Lys Ile Pro Asp Leu Glu Asp Pro Glu Ile Glu Gly Pro Val Gln
                245                 250                 255

Val Ala Arg Arg Ser Asp Met Asp Met Asn Gly His Ile Asn Asn Val
            260                 265                 270

Thr Tyr Leu Gly Trp Ala Leu Glu Thr Val Pro Pro Asp Val Tyr Leu
        275                 280                 285

Asn Tyr Ser Leu His Glu Val Glu Ile Asp Phe Lys Ser Glu Cys Met
    290                 295                 300

Ala Gly Gln Thr Val Glu Ser Ile Gly Ser Arg Ile Lys Glu Asp Thr
305                 310                 315                 320

Asn Gly Thr Gly Ile Leu Arg Phe Val His Leu Leu Arg Arg Cys Asp
                325                 330                 335

Asp Ser Gly Cys Tyr Glu Leu Val Arg Ala Arg Thr Thr Trp Arg Pro
            340                 345                 350

Gln Tyr Gly Lys Leu Gln Leu His
        355                 360

<210> SEQ ID NO 8
<211> LENGTH: 206
<212> TYPE: PRT
<213> ORGANISM: Pseudococcomyxa sp.

<400> SEQUENCE: 8

Gly Arg Leu Thr Asp Asp Gly Thr Ala Phe Leu Glu Glu His Arg Ile
1               5                   10                  15

Arg Gly Tyr Glu Val Gly Pro Asp Gln Lys Thr Thr Ile Val Thr Ile
            20                  25                  30

Ala Asn Leu Leu Gln Glu Val Ala Gly Asn His Ala Val Ala Leu Trp
        35                  40                  45

Gly Arg Thr Asp Ala Gly Tyr Ala Thr Asp Pro Leu Met Val Glu Arg

```
            50              55              60
His Leu Ile Phe Ala Val Thr Arg Met Gln Ile Arg Met Asp Ser Tyr
 65                  70                  75                  80

Pro Lys Trp Gly Asp Leu Val Gln Ile Glu Thr Trp Phe Gln Glu Glu
                     85                  90                  95

Gly Arg Val Ser Ala Cys Arg Asn Trp Ile Leu Thr Asn Gln Ser Thr
                100                 105                 110

Gly Glu Glu Ile Gly Arg Ala Thr Ser Thr Trp Val Met Val Asn Thr
            115                 120                 125

Leu Thr Arg Arg Leu Ser Lys Met Pro Asp Glu Met Arg Ala Lys Met
130                 135                 140

Glu Tyr Leu Ala Pro His Pro Ser Arg Asp Val Leu Pro Ala Ala Glu
145                 150                 155                 160

Val Arg Gln Lys Ile Pro Asp Leu Glu Asp Pro Pro Glu Ile Glu Gly
                165                 170                 175

Pro Val Gln Val Ala Arg Arg Ser Asp Met Asp Met Asn Gly His Ile
                180                 185                 190

Asn Asn Val Thr Tyr Leu Gly Trp Ala Leu Glu Thr Val Pro
            195                 200                 205

<210> SEQ ID NO 9
<211> LENGTH: 2910
<212> TYPE: DNA
<213> ORGANISM: Pseudococcomyxa sp.

<400> SEQUENCE: 9
acgtcagtgc tgctctgatt ttgtgctcta ggcagacacc tgttaagaat caattctgca      60
ttgcaacttt tctggagcca acgttagtca ggctcacgtg atcgatagcg ttgttgcttt     120
tgggcgctcc tccattcccc aaggtttcga gtacaagcaa attttagcac tgatattgtt     180
tgtgacaatt tcagtgatgt atacataatc tggtcagata cttgaagagt tcagcccgcc     240
cactcttgtg cgacgcaccg aacacagtga cagacatctg acatctgtc tacaatgcca      300
gactcattct ggagttgtga accatcata tcagccgatg gcacagaaag cgttgttagt      360
aagacgccaa ggaagaatag ccctgcggaa gaaatggttg ccgtgcttac cctgctgact     420
tggttcgggt gcgcttcctt ctaacgcatc tcatcttgct cttggcaatg caatgcaag      480
ggaaaactgc ttcttaacac ttctcttagg tgcccgcaga aggttgattc atcaatgcga     540
tgcaactttt agagttacct tctcagcact gggaagctgt cctgactgaa gaagcatgct     600
gcatgtgcag atcggtgtgg ctgattccct ggctactgct gtggctattg tttgcgactg     660
tcgcgtgggc ttccaaaatt gcgctcacca cagtgttgat tctcatcgcc ctgagtttcc     720
tgcctgctgg caatgtgcgc cctgattcgg agcctgcgtt gcacagaagg ggatgcataa     780
tattgcatgt atggggccat tgcttgatg agcattacca tgccagtact ggagctgagg      840
gtaatagagt ggctgtgttc tgcctgcaga tatggtgggc atacagaagc ttgccagtgt     900
gggatctatg gaggcgtcgc tttaggtgcg aggtgttttc gctgactttt tccctttaag     960
caagcaaatt ctcaggattg aagggggggtt gtgttccaag tgcagcatgc gcctagtaac    1020
gccacccaag gatcactttc tactgccaga caagaattac ttgtttgcgg gtcagtcctg    1080
gatgcccagt cctctccagc gagcttacgt gctagttttt cagccccgtg aagacacagc    1140
agtgttgtca tggactacac gacctgtgta aaactaatcc atgattggca ttgtgcagag    1200
ttccctcata cagtgtaccc aatgggggtca tggcttggac tgcccctctg tggcaaacaa    1260
```

-continued

| | |
|---|---|
| ggcaccggta agaacagccg tgtcttactt gcccatcaag ggaagttcca tatagaagct | 1320 |
| ggccttcaat ggcaatctct gtaggctgag cagtattgct ggcgagtgtg cagggctgcc | 1380 |
| atacaatctg aggggcggca ttgcaagcat catgttccag ctgcccatcg tgaagcacaa | 1440 |
| ctacgcgtgg gcaggctgca tgccggcagg tgacctgcca cgtcccttcg ctccagatac | 1500 |
| agagtgacat cttgccataa atgtgcagtt ttgtatggcg caaaaccctg tctgcgcaca | 1560 |
| gcgtgaccag cgtttgtggt atcgggcaga gtacaaacgg atgctggcgc acttgaggga | 1620 |
| accgggcgca gctctgagcg tgatcccgga gggcatcgct gggatctttc tggcgcagga | 1680 |
| tacacgggtg gagacgatct tcctgtcaaa gcgcaagggg ttcgtgaggt tgcaatccga | 1740 |
| ggccggggca ggtgagtgcg gattggcgca tcctagttac ttgccgctgg catgcatcct | 1800 |
| ttttctggtg ctgcagaagg gatgcatgca tggttctttc tcatgtctgg ggcttttac | 1860 |
| ttggaattgc tgcagggagg gtatgcctga cagagtgtct ctttgtgcag atctggtgcc | 1920 |
| ggtgtaccac atgggtcaga gccagctgct gacattttgg ggccctgaga agctgtctcg | 1980 |
| aaggtggcga gcttccatcg gcatcttctg gggagcttgg ggcctgccgc tgcccaggaa | 2040 |
| gcatcccatt gtttcccttg tgggcgcacc cattccaggt ggattactac gtttcaatcc | 2100 |
| ttcacctagc tggtgtgcaa cctgcgatgc aatgggggtc cttttggtgg atgctgcttg | 2160 |
| gtgccacaac tgccttcctg cttgctgaaa cgctcgtttg tgttgcagtt aagcaggagg | 2220 |
| atcatccaag ccaggagcag atcgacaaga tccacggtca atttgccgta agtatcaaga | 2280 |
| agttgtttga tgatcacaag caccttttgg gaccgcattg ggcccagaag gagctccaga | 2340 |
| taatgtgaga tgaacaccag caaggcggtg ctgcgcattg cagggctgtg aggatttctt | 2400 |
| acctgcagtt ttcaagctga tcaggagatt tgtgattgcg gatggatgtg agagaacgct | 2460 |
| gtagcatagt agccgtagat aagtcagctg gagtgccttg caatgacctg tgatatcacc | 2520 |
| atgtggatct tctcttgcac tcttttggct ggtgacctgt attatttcgt acagcgacgg | 2580 |
| ggagtgagcc tcctccctga gctttggaca gatgaggatt gttttttact tttagtgctg | 2640 |
| ccattaagca caagaagcat agcacggaca tcatagcaga ctgcaactag cagttcaata | 2700 |
| cctgctacta gcagtgggat atatctgtgc atgggatagg acgtgggaga aggtggtatt | 2760 |
| ttgcaagaga atgttgttcg aacttgtctg tacaacctcg caaggggctg gtgcaatgtg | 2820 |
| acaccatgat gagcatgcat ggtgtgctcc atgtgggggg acctcaggca cctcgcaaaa | 2880 |
| gaagcatgca gtcaatattc ctggtaacga | 2910 |

<210> SEQ ID NO 10
<211> LENGTH: 1014
<212> TYPE: RNA
<213> ORGANISM: Pseudococcomyxa sp.
<220> FEATURE:
<221> NAME/KEY: CDS
<222> LOCATION: (1)..(1014)

<400> SEQUENCE: 10

```
aug cca gac uca uuc ugg agu ugu gaa acc auc aua uca gcc gau ggc      48
Met Pro Asp Ser Phe Trp Ser Cys Glu Thr Ile Ile Ser Ala Asp Gly
1               5                   10                  15 aca gaa agc guu guu agu aag acg cca agg aag aau agc ccu gcg gaa      96
Thr Glu Ser Val Val Ser Lys Thr Pro Arg Lys Asn Ser Pro Ala Glu
            20                  25                  30 gaa aug guu gcc gug cuu acc cug cug acu ugg uuc gga ucg gug ugg     144
Glu Met Val Ala Val Leu Thr Leu Leu Thr Trp Phe Gly Ser Val Trp
        35                  40                  45
```

| | |
|---|---|
| cug auu ccc ugg cua cug cug ugg cua uug uuu gcg acu guc gcg ugg<br>Leu Ile Pro Trp Leu Leu Leu Trp Leu Leu Phe Ala Thr Val Ala Trp<br>50                                    55                             60 | 192 |
| gcu ucc aaa auu gcg cuc acc aca gug uug auu cuc auc gcc cug agu<br>Ala Ser Lys Ile Ala Leu Thr Thr Val Leu Ile Leu Ile Ala Leu Ser<br>65                     70                            75                       80 | 240 |
| uuc cug ccu gcu ggc aau aua ugg ugg gca uac aga agc uug cca gug<br>Phe Leu Pro Ala Gly Asn Ile Trp Trp Ala Tyr Arg Ser Leu Pro Val<br>                          85                            90                       95 | 288 |
| ugg gau cua ugg agg cgu cgc uuu agc aug cgc cua gua acg cca ccc<br>Trp Asp Leu Trp Arg Arg Arg Phe Ser Met Arg Leu Val Thr Pro Pro<br>                    100                         105                        110 | 336 |
| aag gau cac uuu cua cug cca gac aag aau uac uug uuu gcg gag uuc<br>Lys Asp His Phe Leu Leu Pro Asp Lys Asn Tyr Leu Phe Ala Glu Phe<br>               115                         120                         125 | 384 |
| ccu cau aca gug uac cca aug ggg uca ugg cuu gga cug ccc cuc ugu<br>Pro His Thr Val Tyr Pro Met Gly Ser Trp Leu Gly Leu Pro Leu Cys<br>130                                 135                            140 | 432 |
| ggc aaa caa ggc acc ggg cug cca uac aau cug agg ggc ggc auu gca<br>Gly Lys Gln Gly Thr Gly Leu Pro Tyr Asn Leu Arg Gly Gly Ile Ala<br>145                          150                            155                       160 | 480 |
| agc auc aug uuc cag cug ccc auc gug aag cac aac uac gcg ugg gca<br>Ser Ile Met Phe Gln Leu Pro Ile Val Lys His Asn Tyr Ala Trp Ala<br>                    165                         170                        175 | 528 |
| ggc ugc aug ccg gca gag uac aaa cgg aug cug gcg cac uug agg gaa<br>Gly Cys Met Pro Ala Glu Tyr Lys Arg Met Leu Ala His Leu Arg Glu<br>                       180                         185                        190 | 576 |
| ccg ggc gca gcu cug agc gug auc ccg gag ggc auc gcu ggg auc uuu<br>Pro Gly Ala Ala Leu Ser Val Ile Pro Glu Gly Ile Ala Gly Ile Phe<br>               195                         200                         205 | 624 |
| cug gcg cag gau aca cgg gug gag acg auc uuc cug uca aag cgc aag<br>Leu Ala Gln Asp Thr Arg Val Glu Thr Ile Phe Leu Ser Lys Arg Lys<br>210                               215                            220 | 672 |
| ggg uuc gug agg uug gca auc cag gcc ggg gca gau cug gug ccg gug<br>Gly Phe Val Arg Leu Ala Ile Gln Ala Gly Ala Asp Leu Val Pro Val<br>225                               230                            235                       240 | 720 |
| uac cac aug ggu cag agc cag cug cug aca uuu ugg ggc ccu gag aag<br>Tyr His Met Gly Gln Ser Gln Leu Leu Thr Phe Trp Gly Pro Glu Lys<br>                    245                         250                        255 | 768 |
| cug ucu cga agg ugg cga gcu ucc auc ggc auc uuc ugg gga gcu ugg<br>Leu Ser Arg Arg Trp Arg Ala Ser Ile Gly Ile Phe Trp Gly Ala Trp<br>                       260                         265                        270 | 816 |
| ggc cug ccg cug ccc agg aag cau ccc auu guu ucc cuu gug ggc gca<br>Gly Leu Pro Leu Pro Arg Lys His Pro Ile Val Ser Leu Val Gly Ala<br>               275                         280                         285 | 864 |
| ccc auu cca guu aag cag gag gau cau cca agc cag gag cag auc gac<br>Pro Ile Pro Val Lys Gln Glu Asp His Pro Ser Gln Glu Gln Ile Asp<br>290                               295                            300 | 912 |
| aag auc cac ggu caa uuu gcc gua agu auc aag aag uug uuu gau gau<br>Lys Ile His Gly Gln Phe Ala Val Ser Ile Lys Lys Leu Phe Asp Asp<br>305                               310                            315                       320 | 960 |
| cac aag cac cuu uug gga ccg cau ugg gcc cag aag gag cuc cag aua<br>His Lys His Leu Leu Gly Pro His Trp Ala Gln Lys Glu Leu Gln Ile<br>               325                         330                         335 | 1008 |
| aug uga<br>Met | 1014 |

<210> SEQ ID NO 11
<211> LENGTH: 337
<212> TYPE: PRT

<213> ORGANISM: Pseudococcomyxa sp.

<400> SEQUENCE: 11

```
Met Pro Asp Ser Phe Trp Ser Cys Glu Thr Ile Ile Ser Ala Asp Gly
1               5                   10                  15
Thr Glu Ser Val Val Ser Lys Thr Pro Arg Lys Asn Ser Pro Ala Glu
                20                  25                  30
Glu Met Val Ala Val Leu Thr Leu Leu Thr Trp Phe Gly Ser Val Trp
            35                  40                  45
Leu Ile Pro Trp Leu Leu Leu Trp Leu Leu Phe Ala Thr Val Ala Trp
        50                  55                  60
Ala Ser Lys Ile Ala Leu Thr Thr Val Leu Leu Ile Ala Leu Ser
65                  70                  75                  80
Phe Leu Pro Ala Gly Asn Ile Trp Trp Ala Tyr Arg Ser Leu Pro Val
                85                  90                  95
Trp Asp Leu Trp Arg Arg Arg Phe Ser Met Arg Leu Val Thr Pro Pro
            100                 105                 110
Lys Asp His Phe Leu Leu Pro Asp Lys Asn Tyr Leu Phe Ala Glu Phe
        115                 120                 125
Pro His Thr Val Tyr Pro Met Gly Ser Trp Leu Gly Leu Pro Leu Cys
    130                 135                 140
Gly Lys Gln Gly Thr Gly Leu Pro Tyr Asn Leu Arg Gly Gly Ile Ala
145                 150                 155                 160
Ser Ile Met Phe Gln Leu Pro Ile Val Lys His Asn Tyr Ala Trp Ala
                165                 170                 175
Gly Cys Met Pro Ala Glu Tyr Lys Arg Met Leu Ala His Leu Arg Glu
            180                 185                 190
Pro Gly Ala Ala Leu Ser Val Ile Pro Glu Gly Ile Ala Gly Ile Phe
        195                 200                 205
Leu Ala Gln Asp Thr Arg Val Glu Thr Ile Phe Leu Ser Lys Arg Lys
    210                 215                 220
Gly Phe Val Arg Leu Ala Ile Gln Ala Gly Ala Asp Leu Val Pro Val
225                 230                 235                 240
Tyr His Met Gly Gln Ser Gln Leu Leu Thr Phe Trp Gly Pro Glu Lys
                245                 250                 255
Leu Ser Arg Arg Trp Arg Ala Ser Ile Gly Ile Phe Trp Gly Ala Trp
            260                 265                 270
Gly Leu Pro Leu Pro Arg Lys His Pro Ile Val Ser Leu Val Gly Ala
        275                 280                 285
Pro Ile Pro Val Lys Gln Glu Asp His Pro Ser Gln Glu Gln Ile Asp
    290                 295                 300
Lys Ile His Gly Gln Phe Ala Val Ser Ile Lys Lys Leu Phe Asp Asp
305                 310                 315                 320
His Lys His Leu Leu Gly Pro His Trp Ala Gln Lys Glu Leu Gln Ile
                325                 330                 335
Met
```

<210> SEQ ID NO 12
<211> LENGTH: 200
<212> TYPE: PRT
<213> ORGANISM: Pseudococcomyxa sp.

<400> SEQUENCE: 12

```
Tyr Leu Phe Ala Glu Phe Pro His Thr Val Tyr Pro Met Gly Ser Trp
1               5                   10                  15
```

Leu Gly Leu Pro Leu Cys Gly Lys Gln Gly Thr Gly Leu Pro Tyr Asn
        20                  25                  30

Leu Arg Gly Gly Ile Ala Ser Ile Met Phe Gln Leu Pro Ile Val Lys
        35                  40                  45

His Asn Tyr Ala Trp Ala Gly Cys Met Pro Ala Glu Tyr Lys Arg Met
 50                  55                  60

Leu Ala His Leu Arg Glu Pro Gly Ala Ala Leu Ser Val Ile Pro Glu
 65                  70                  75                  80

Gly Ile Ala Gly Ile Phe Leu Ala Gln Asp Thr Arg Val Glu Thr Ile
                85                  90                  95

Phe Leu Ser Lys Arg Lys Gly Phe Val Arg Leu Ala Ile Gln Ala Gly
            100                 105                 110

Ala Asp Leu Val Pro Val Tyr His Met Gly Gln Ser Gln Leu Leu Thr
        115                 120                 125

Phe Trp Gly Pro Glu Lys Leu Ser Arg Arg Trp Arg Ala Ser Ile Gly
130                 135                 140

Ile Phe Trp Gly Ala Trp Gly Leu Pro Leu Pro Arg Lys His Pro Ile
145                 150                 155                 160

Val Ser Leu Val Gly Ala Pro Ile Pro Val Lys Gln Glu Asp His Pro
                165                 170                 175

Ser Gln Glu Gln Ile Asp Lys Ile His Gly Gln Phe Ala Val Ser Ile
            180                 185                 190

Lys Lys Leu Phe Asp Asp His Lys
            195                 200

<210> SEQ ID NO 13
<211> LENGTH: 648
<212> TYPE: DNA
<213> ORGANISM: Pseudococcomyxa sp.

<400> SEQUENCE: 13
tgtaatggcc atatcgaagc actgttctgg aaatctattc aagtttgagg acaaaaatgc      60
atcattagac cgcagtctga cgtgccctga agcctgagcc tgacatgtga tgcctcgtcg     120
tgcaacaaat cgtggcgggt gaacagcgct atttaaaaga agagccagct caaactgact     180
cctgtttata ggatattcat gataaggaat cagaatcact ttccacacac caaagtgatc     240
tagtactgcc gcaagatcaa aactcgtgga agagtgcaag accgcgcttg caagaatca      300 caatagccca atgctttcag tagcagacaa ctcttaagtg ctaatttgct gcccacaatt     360
tccggggctg gagtttcaga gcattccaga cgccacttgc cagatttggc tccatcaggg     420
aactggaaca tcgagagagc tctctgtcaa gccgcctctc ctgcccacca gcaaagtat      480 cctttggcat ccaacctttg gtacctctgt cacaggtgtg gttgctttcc gagccgtcta     540 acgtctttc tgtctgaaag cgaggtggtt tttgtgttgc gcttgccaca gaaaggcttg     600
gtgcaagtga tctgaccagc ttatctgttt gcaggaaaac tcgccacc                 648

<210> SEQ ID NO 14
<211> LENGTH: 694
<212> TYPE: DNA
<213> ORGANISM: Pseudococcomyxa sp.

<400> SEQUENCE: 14
accgctgaga gctgcgtgag gatctggggt aggagctgtg cagcctctgc cgctgctggc      60
ccctgctgtt gtacacaagt gccgcccgcc cagcgggagg tgctcggacc ctgctggcat     120

```
gccttggttg ctaggcaggc tcagaactgg gtgctggact ttaggtggcg tggcttcacg        180
cagctccttg tctgagcagg gcttctgccc tgcggcgtgt gcgcctttct gtgtgcatcc        240
cccggatctc tccgttgcag tacttgtcag cagtctctct tttccctgtc agtaggatag        300
gccagagcta ctccggcttc catcaaacat tttggaactt ttcatcctgc gcttcttgtc        360
ttcacgatcc taggatgtgt ggtggggatg atacgctttg tattcacaca ctcgagttca        420
acaactttct tagggtgttc aactggggag gggcattgtg accatcctga cagacataca        480
tctcacacgt caaagagggc ttgaaaagga gtgcatatgc atgtgcatat cctgtggttg        540
ttgagactac aggaagagtg taaagggttc aactcacaag aaaagtttct gtggaagcag        600
tgcgtcagtg catgcatgga ctgagttaag agccgcaggt tgtcacacac ttcacatcct        660
gttgtttaga agcatcatgt ttgcaagcac tcgc                                    694

<210> SEQ ID NO 15
<211> LENGTH: 280
<212> TYPE: DNA
<213> ORGANISM: Pseudococcomyxa sp.

<400> SEQUENCE: 15
gtacgcagct ttcctatacc ctcaccgcgt gtggttcaca aaggtttctg gctaaggata         60
gccacatgag acttccctta cacccagaaa gcagatgcac cccatatttc gggcagtcaa        120
tgtgctttgc tttcctttgt agaggccctg cagtgttgcg gactgccctc cagtgttctg        180
aagtgttctt tctttcaggg tgcaatttta ctttatccat tgtctatctg tcctgtgttg        240
ggcaagaggg actgacgctg cgctgttttg tttttgcag                               280
```

GENETICALLY MODIFIED STRAIN OF EUKARYOTIC MICROALGA HAVING IMPROVED TRIGLYCERIDE PRODUCTIVITY, AND USE THEREOF

CROSS-REFERENCE TO RELATED APPLICATIONS

This application is based on a 371 of PCT/JP2016/075875, filed Sep. 2, 2016, which claims benefit of Japanese Patent Application No. 2015-173161 filed on Sep. 2, 2015.

TECHNICAL FIELD

The present invention relates to the eukaryotic microalgae, which have been genetically modified such that larger amounts of assimilation products produced by photosynthesis are directed to the synthesis of triglyceride (=triacylglycerol; hereinafter referred to as "TAG"), and the use thereof.

BACKGROUND ART

Studies regarding production of industrial products such as biodiesel fuel and/or food products by using, as raw materials, compounds including fatty acid produced by unicellular photosynthetic organisms (hereinafter referred to as "microalgae") or TAG that releases fatty acid as a result of hydrolysis (which are collectively referred to as "lipids"), have been conducted over the world. However, under the current circumstances, lipid production costs are high, and thus, it is difficult to produce biodiesel fuel and the like on the commercial basis (Non Patent Literature 1). Hence, further technical developments for reducing the production costs of biodiesel fuel and the like have been continued, and one of such technical developments is a study regarding the improvement of the TAG productivity of microalgae.

A majority of microalgae accumulate a part of assimilation products generated as a result of photosynthesis in the form of starch or TAG. The accumulated amounts of such starch and TAG are different depending on the types of microalgae, and are also different depending on culture conditions although they are produced from the same type of organism. This is considered because the speed of converting photosynthetic assimilation products to starch and TAG and the speed of decomposing once synthesized storage substances are different, depending on organism species and culture conditions, and because it appears as a difference in the accumulated amounts of starch and TAG.

Raw materials for TAG are glycerol-3-phosphate and fatty acid. Glycerol-3-phosphate is synthesized from glycerol and ATP as substrates, by the action of glycerol kinase. On the other hand, fatty acid is biosynthesized in a chloroplast.

The initial reaction of fatty acid biosynthesis is catalyzed by acyl-CoA carboxylase, and malonyl-CoA is produced from acetyl-CoA. Malonyl-CoA reacts with an acyl carrier protein (ACP) to produce malonyl-ACP. Malonyl-ACP reacts with acyl-ACP prepared by binding an acyl group with ACP (C=2: acetyl-ACP, C=4: butyryl-ACP, etc.) to extend two carbon chains of acyl-ACP. When this extension reaction is repeated so that the length of carbon chains of acyl groups becomes (most commonly) 16, the acyl-ACP is hydrolyzed to palmitic acid (C16:0) and ACP by the action of acyl-ACP thioesterase. Palmitic acid binds to CoA to become palmityl-CoA, and the palmityl-CoA transfers from the chloroplast to endoplasmic reticulum. Very long chain fatty acid elongase and fatty acid desaturase further act on the palmityl-CoA, so as to produce a CoA ester of oleic acid that is monovalent unsaturated fatty acid (oleyl-CoA:C18:1). Palmitic acid and oleic acid are fatty acids that are contained in the highest contents in many organisms.

Biosynthesis of TAG is carried out on the endoplasmic reticulum membrane. First, by the action of glycerol-3-phosphate acyltransferase, an acyl group of acyl-CoA is added to the sn-1 position of glycerol-3-phosphate, so as to generate lysophosphatidic acid. Subsequently, by the action of acylglycerophosphate acyltransferase, an acyl group of acyl-CoA is added to the sn-2 position of lysophosphatidic acid, so as to generate phosphatidic acid. Phosphatidic acid is dephospharylated by phosphatidate phosphatase, and is converted to diacylglycerol. Thereafter, by the action of diacylglycerol acyltransferase (DGAT), TAG is synthesized from the diacylglycerol. DGAT is classified into two families each having a different evolutionary origin, and thus, the two DGATs are referred to as DGAT1 and DGAT2, respectively. This pathway of synthesizing TAG from glycerol-3-phosphate and acyl-CoA is referred to as a Kennedy pathway for TGA synthesis.

TAG is also synthesized by reactions other than this Kennedy pathway. An example is the following reaction involving phospholipid:diacylglycerol acyltransferase:

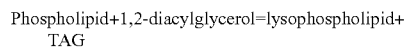

Phospholipid+1,2-diacylglycerol=lysophospholipid+TAG

Several studies have already been conducted to increase enzyme activity associated with the TAG synthesis according to a genetic recombination technique, and to improve the amount of TAG produced per unit time and per unit light-receiving area of microalgae (hereinafter referred to as "TAG productivity"), so as to contribute to a reduction in the biodiesel production costs.

A large number of reports have been made regarding that TAG productivity is increased by allowing a gene encoding DGAT that is the last enzyme in the above-described Kennedy pathway to express at a high level. For example, by introducing a DGAT gene derived from the Gram-negative bacterium Acinetobacler into a *Synechococcus elongatus* PCC 7942 strain belonging to Cyanobacteria, the *Synechococcus* became to accumulate approximately two times the amount of TAG (Patent Literature 1).

Patent Literature 2 discloses that a gene encoding DGAT, phospholipid: diacylglycerol acyltransferase or phosphatidic acid phosphatase is introduced into *Nannochloropsis* belonging to Heterokontophyta, Eustigmataceae, so as to increase the content of TAG. However, this patent literature does not describe details of the effects of such gene introduction in the Examples thereof.

A DGAT1 gene derived from various organisms having a Pleckstrin-homology domain was introduced into *Nannochloropsis*, and as a result, the content of lipids in the transformed strain was increased in comparison to that in a wild-type strain (Patent Literature 3).

A mouse-derived DGAT was introduced into *Nannochloropsis*, and as a result, the content of TAG was increased (Patent Literature 4).

The above-mentioned plurality of DGAT2 genes (homologous genes) are present in *Chlamydomonas reinhardtii* belonging to Viridiplantae, Chlorophyta (hereinafter referred to as "green algae"). Although these homologous genes were allowed to highly express in *Chlamydomonas reinhardtii*, an increase in the content of lipids was not observed. On the other hand, when one of the DGAT2 homologous genes of *Chlamydomonas reinhardtii* was allowed to express in yeast, the transformed yeast exhibited higher TAG productivity than the wild-type yeast (Non Patent Literature 2).

When DGAT2 of *Phaeodactylum tricornutum* belonging to Heterokontophyta, Bacillariophyceae was cloned and the obtained clones were then allowed to highly express in the same strain, the TAG productivity of this strain was increased (Non Patent Literatures 3 and 4).

A gene encoding the initial enzyme of the Kennedy pathway for TAG synthesis, glycerol-3-phosphate acyltransferase, was separated from the green algae *Lobosphaera incisa*, and thereafter, it was introduced into *Chlamydomonas reinhardtii* and was allowed to express therein, and as a result, TAG productivity was significantly increased (Non Patent Literature 5).

Moreover, glycerol kinase that synthesizes glycerol-3-phosphate as a substrate of the above-described glycerol-3-phosphate acyltransferase was allowed to highly expressed in the diatom Fistulifera solaris JPCC DA0580 strain, and as a result, TAG productivity was slightly increased (Non Patent Literature 6).

On the other hand, it has been reported that, when an acetyl-CoA carboxylase gene and an acyl-ACP thioesterase gene that are initial enzymes for fatty acid synthesis are allowed to highly expressed in *Escherichia coli*, the content of free fatty acid is increased (Non Patent Literature 7).

However, in many studies, such an acyl-ACP thioesterase gene has been used to promote the synthesis of, not fatty acids (C16 and C18) having a carbon chain with a common length, but relatively short fatty acids (C10, C12 and C14). It has been clarified that lipids including fatty acids such as C10 or C12 are accumulated in seeds of the plant of the family Lauraceae, *Umbellularia californica*, and that such accumulation is caused by acyl-ACP thioesterase that hydrolyzes acyl-ACP having a C12 carbon chain of this plant. When the cDNA of the acyl-ACP thioesterase gene of *U. californica* having the substrate specificity of hydrolyzing relatively short fatty acids was introduced into *Escherichia coli* and was allowed to highly express therein, free fatty acids of C12 and C14 were synthesized and were then discharged to outside of the cells (Non Patent Literature 8).

Studies regarding that a gene encoding acyl-ACP thioesterase and a gene encoding diacylglycerol acyltransferase (DGAT2) are introduced into the green algae *Chlamydomonas reinhardtii*, so as to increase the rate of the C12 fatty acid have been disclosed (Patent Literature 5). However, the accumulation of TAG per dry weight of this recombinant was found to be at maximum approximately 2%, and even if free fatty acids were included, the accumulation of TAG was 7% or less.

By the way, *Pseudococcomyxa* sp. KJ strain belonging to the green algae Trebouxiophyceae (hereinafter referred to as "KJ strain") is unicellular green algae having extremely high TAG productivity, which has been separated from hot spring water (Patent Literature 6), and the KJ strain can be cultured in the open culture system disclosed in Patent Literature 7.

CITATION LIST

Patent Literature

Patent Literature 1: U.S. Pat. No. 8,394,614 B2
Patent Literature 2: U.S. Pat. No. 8,722,359 B2
Patent Literature 3: U.S. Pat. No. 8,835,149 B2
Patent Literature 4: US 2014/0106417 A1
Patent Literature 5: JP Patent Publication (Kokai) No. 2014-14334 A
Patent Literature 6: JP Patent Publication (Kokai) No. 2015-015918 A
Patent Literature 7: JP Patent Publication (Kokai) No. 2014-117202 A Non Patent Literature Non Patent Literature 1: Quinn J C, Davis R. (2015) The potentials and challenges of algae based biofuels: a review of the techno-economic, life cycle, and resource assessment modeling. Bioresour Technol. 184: 444-452.
Non Patent Literature 2: Hung C-H, Ho M-Y, Kanehara K, Nakamura Y. (2013) Functional study of diacylglycerol acyltransferase type 2 family in *Chlamydomonas reinhardtii*. FEBS Lett. 587: 2364-2370.
Non Patent Literature 3: Niu Y-F, Zhang M-H, Li D-W, Yang W-D, Liu J-S, Bai W-B, Li H-Y. (2013) Improvement of neutral lipid and polyunsaturated fatty acid biosynthesis by overexpressing a type 2 diacylglycerol acyltransferase in marine diatom *Phaeodactylum tricornutum*. Mar. Drugs 11: 4558-4569.
Non Patent Literature 4: Xue J, Niu Y F, Huang T, Yang W D, Liu J S, Li H Y. (2015) Genetic improvement of the microalga *Phaeodactylum tricornutum* for boosting neutral lipid accumulation. Metab Eng. 27: 1-9.
Non Patent Literature 5: Iskandarov U, Sitnik S, Shtaida N, Didi-Cohen S. Leu S, Khozin-Goldberg I, Cohen Z, Boussiba S. (2015) Cloning and characterization of a GPAT-like gene from the microalga *Lobosphaera incisa* (Trebouxiophyceae): overexpression in *Chlamydomonas reinhardtii* enhances TAG production. J Appl Phycol DOI 10.1007/sl0811-015-0634-1.
Non Patent Literature 6: Muto M, Tanaka M, Liang Y, Yoshino T, Matsumoto M, Tanaka T. (2015) Enhancement of glycerol metabolism in the oleaginous marine diatom Fistulifera solaris JPCC DA0580 to improve triacylglycerol productivity. Biotechnol Biofuels. 8(1): 4. doi: 10.1186/s13068-014-0184-9.
Non Patent Literature 7: Davis M S, Solbiati J, Cronan J E Jr. (2000) Overproduction of acetyl-CoA carboxylase activity increases the rate of fatty acid biosynthesis in *Escherichia coli*. J Biol Chem. 275: 28593-28598.
Non Patent Literature 8: Voelker T A, Davies H M. Alteration of the specificity and regulation of fatty acid synthesis of *Escherichia coli* by expression of a plant medium-chain acylacyl Carrier protein thioesterase. J Bacteriol 1994; 176: 7320-7327.

SUMMARY OF INVENTION

Technical Problem

As mentioned above, the KJ strain is suitable for mass culture performed out of doors, and it can be said that the KJ strain is one of the most promising strains as raw materials for commercial production of lipids. However, it has been desired to further improve the TAG productivity of the KJ strain and to reduce the production costs of TAG.

Hence, it is an object of the present invention to produce eukaryotic microalgae including the KJ strain, having improved TAG productivity, according to genetic manipulation, and to provide a method for producing TAG, in which the genetically modified strain of eukaryotic microalgae is utilized.

Solution to Problem

As a result of intensive studies conducted to achieve the aforementioned object, the present inventors have found that the expression of three genes in a KJ strain, namely, (i) a gene encoding alpha-glucosidase (AGL1) associated with decomposition of starch, (ii) a gene encoding acyl-ACP thioesterase (FAT1) that hydrolyzes fatty acid synthesized as acyl-ACP in the chloroplast and supplies the fatty acid to the TAG synthetic pathway on the endoplasmic reticulum, and (iii) one (DGAT2d) of homologous genes encoding DGAT2 that is an enzyme at the final stage of the TAG synthetic pathway, is most strongly induced at the time of TAG synthesis. Moreover, the present inventors have cloned these three genes downstream of a suitable promoter and have then introduced them into the KJ strain. As a result, the TAG productivity of the transformed strain has been significantly improved, thereby completing the present invention. These three genes are enzymes that are broadly associated with the metabolism of photosynthetic assimilation products of microalgae. Thus, it is considered that the aforementioned results obtained regarding the KJ strain can be reproduced even in many of other eukaryotic microalgae.

Specifically, the present invention includes the following:
(1) A genetically modified strain of eukaryotic microalgae, in which a gene encoding an AGL1 protein is highly expressed, wherein
TAG productivity is improved in comparison to a parent strain thereof, and
the AGL1 protein has an amino acid sequence having sequence identity of at least 50% with the amino acid sequence shown in SEQ ID NO: 4, and has alpha-glucosidase activity.
(2) The genetically modified strain of eukaryotic microalgae according to the above (1), in which a gene encoding an FAT1 protein and/or a gene encoding a DGAT2 protein are also highly expressed, wherein
the FAT1 protein has an amino acid sequence having sequence identity of at least 50% with the amino acid sequence shown in SEQ ID NO: 8, and has acyl-ACP thioesterase activity, and the DGAT2 protein has an amino acid sequence having sequence identity of at least 50% with the amino acid sequence shown in SEQ ID NO: 12, and has diacylglycerol acyltransferase activity.
(3) The genetically modified strain of eukaryotic microalgae according to the above (1) or (2), wherein the genes are operably linked to a promoter ensuring the high expression of the genes.
(4) The genetically modified strain of eukaryotic microalgae according to any one of the above (1) to (3), which belongs to the class Trebouxiophyceae.
(5) The genetically modified strain of eukaryotic microalgae according to the above (4), which belongs to genus *Coccomyxa* or genus *Pseudococcomyxa*.
(6) The genetically modified strain of eukaryotic microalgae according to any one of the above (1) to (5), wherein the genes are derived from a strain belonging to green algae.
(7) The genetically modified strain of eukaryotic microalgae according to the above (6), wherein the genes are derived from a strain belonging to the class Trebouxiophyceae.
(8) The genetically modified strain of eukaryotic microalgae according to the above (7), wherein the genes are derived from a strain belonging to genus *Coccomyxa* or genus *Pseudococcomyxa*.
(9) A method for producing TAG, comprising a step of culturing the genetically modified strain of eukaryotic microalgae according to any one of the above (1) to (8).

The present description includes part or all of the contents as disclosed in Japanese Patent Application No. 2015-173161, which is a priority document of the present application.

Advantageous Effects of Invention

According to the present invention, it becomes possible to produce a genetically modified strain of eukaryotic microalgae having improved TAG productivity. In addition, by culturing the genetically modified strain of eukaryotic microalgae according to the present invention, it becomes possible to significantly reduce the production costs of lipids to be used in biofuel or the like.

BRIEF DESCRIPTION OF DRAWINGS

FIG. 6-1 includes graphs showing the TAG content (% DW) per cell dry weight, the starch content (% DW) per cell dry weight, the cell dry weight (g/L), the TAG production amount (g/L) per culture medium and the TAG productivity (%), of the KJ strain and six pFAT1 plasmid-transformed strains (KJoxFAT1-313, 325, 428, 520, 585, and 643).
FIG. 6-2 is a continuation from FIG. 6-1.
FIG. 6-3 is a continuation from FIG. 6-2.
FIG. 7-1 includes graphs showing the TAG content (% DW) per cell dry weight, the starch content (% DW) per cell dry weight, the cell dry weight (g/L), the TAG production amount (g/L) per culture medium and the TAG productivity (%), which were obtained on Day 7 (7d) and Day 14 (14d) of the culture of the KJ strain and four pDGAT2d plasmid-transformed strains (KJoxDGAT2d-567, 5617, 5650, and 5822).
FIG. 7-2 is a continuation from FIG. 7-1.
FIG. 7-3 is a continuation from FIG. 7-2.
FIG. 9-1 includes graphs showing the mean value and standard error (n=3) of the TAG content (% DW) per cell dry weight, the starch content (% DW) per cell dry weight, the cell dry weight (g/L), the TAG production amount (g/L) per culture medium, and the TAG productivity per day (g/L/d), of the KJ strain, the KJoxFD-2643 strain (KJFAT1 cDNA and KJDGAT2d high expression strain), the KJoxAGL1-6060 strain (KJAGL1 cDNA high expression strain), and the KJoxAFD-41417 strain (KJAGL1 cDNA, KJFAT1 cDNA and KJDGAT2d high expression strain).

FIG. 9-2 is a continuation from FIG. 9-1.
FIG. 9-3 is a continuation from FIG. 9-2.

DESCRIPTION OF EMBODIMENTS

Figure 1:
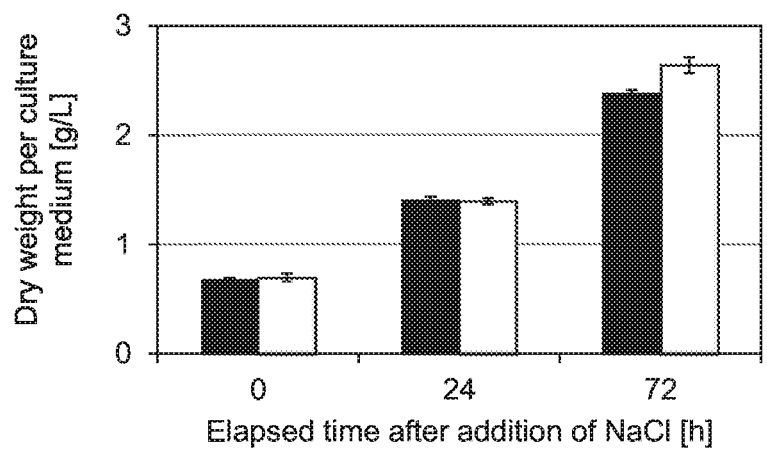
FIG. 1 includes graphs showing proliferation of the KJ strain by culture after addition of 100 mM NaCl, and changes in the contents of TAG and starch.
Figure 1:
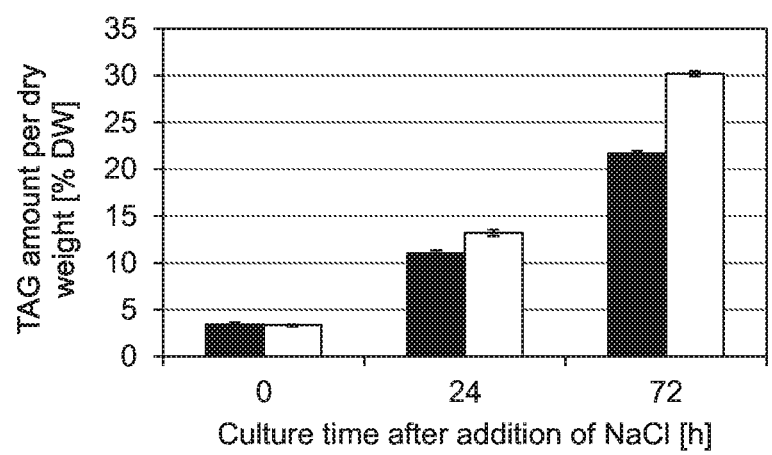
Figure 1:
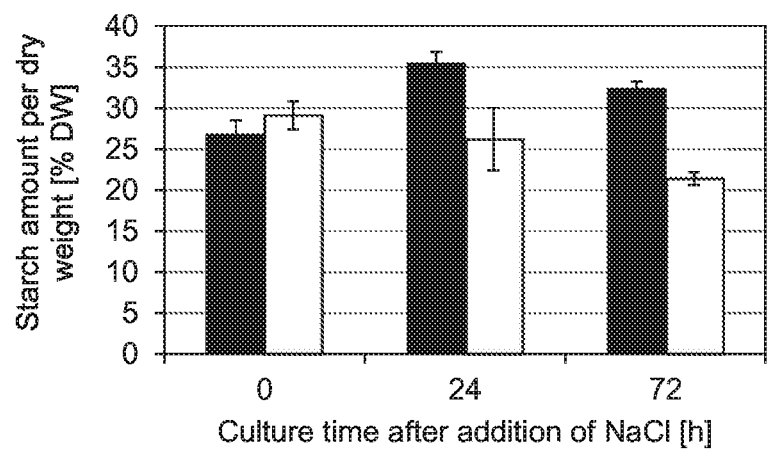

The present invention relates to a genetically modified strain of eukaryotic microalgae, the TAG productivity of which has been significantly improved (for example, 15% or more, preferably 30% or more, and particularly preferably 45% or more) in comparison to the parent strain thereof, as a result that an AGL1 gene, or further, a FAT1 gene and/or a DGAT2 gene as well as the AGL1 gene are introduced into a wild-type eukaryotic microalga strain or a mutant strain derived from the wild-type strain (hereinafter, a strain to which a gene(s) are to be introduced is referred to as a "parent strain").

The most important object for reducing the production costs of biofuel and the like using eukaryotic microalga-derived TAG as a raw material is significant improvement of the TAG productivity of eukaryotic microalgae. The present inventors have found that the TAG productivity of this green alga can be significantly improved by allowing genes encoding a KJ strain-derived AGL1 protein, FAT1 protein and/or DGAT2 protein to highly express in the KJ strain, thereby completing the present invention.

Based on the above-described findings, by allowing an AGL1 gene, or further, a FAT1 gene and/or a DGAT2 gene as well as such an AGL1 gene (hereinafter these genes are collectively referred to as "the gene according to the present invention" at times) to highly express according to gene manipulation, it becomes possible to improve the TAG productivity of eukaryotic microalgae, and also to culture such a TAG productivity-improved strain, so as to significantly reduce the costs of producing TAG that is to be used for biofuel and the like.

In the present invention, examples of the eukaryotic microalgae include eukaryotic microalgae belonging to green algae, diatom (diatom or Bacillariophyceae), Eustigmatophyceae, etc.

The green algae are, for example, green algae belonging to the class Trebouxiophyceae. Examples of the green algae belonging to the class Trebouxiophyceae include green algae belonging to genus *Trebouxia*, genus *Chlorella*, genus *Botryococcus*, genus *Choricystis*, genus *Coccomyxa*, and genus *Pseudococcomyxa*. A specific strain belonging to the class Trebouxiophyceae is a KJ strain. The KJ strain was deposited with the National Institute of Technology and Evaluation, Information on International Patent Organism Depositary (NITE-IPOD) (2-5-8-120, Kazusa Kamatari, Kisarazu-shi, Chiba-ken, Japan, postal code: 292-0818) under Accession No. FERM P-22254 on Jun. 4, 2013. Thereafter, this strain was transferred to an international deposition under the provisions of the Budapest Treaty under Accession No. FERM BP-22254.

Examples of green algae other than the green algae belonging to the class Trebouxiophyceae include green algae belonging to genus *Tetraselmis*, genus *Ankistrodesmus*, genus *Dunaliella*, genus *Neochloris*, genus *Chlamydomonas*, and genus *Scenedesmus*.

Examples of the diatom include eukaryotic microalgae belonging to genus *Fistulifera*, genus *Phaeodactylum*, genus *Thalassiosira*, genus *Cyclotella*, genus *Cylindrotheca*, and genus *Skeletonema*. Further, an example of the Eustigmatophyceae is genus *Nannochloropsis*.

In the present invention, using the aforementioned eukaryotic microalga as a parent strain, and by allowing the gene according to the present invention to highly express therein, the genetically modified strain of eukaryotic microalgae according to the present invention can be obtained.

In the present invention, examples of the AGL1 gene include a KJ strain-derived AGL1 gene (the nucleotide sequence of the gene: SEQ ID NO: 1, the nucleotide sequence of the mRNA: SEQ ID NO: 2, and the amino acid sequence: SEQ ID NO: 3) and a homolog thereof. A specific example of the AGL1 gene is a gene encoding a protein, which has an amino acid sequence having sequence identity of at least 50%, preferably at least 65%, particularly preferably at least 80%, most preferably at least 85%, at least 90%, at least 95%, and 100%, with the amino acid sequence shown in SEQ ID NO: 4 (i.e., a highly conserved amino acid sequence corresponding to an amino acid sequence at positions 215 to 783 in SEQ ID NO: 3), and also has alpha-glucosidase activity. In addition, another specific example of the AGL1 gene is a gene encoding a protein, which has an amino acid sequence having sequence identity of at least 50%, preferably at least 65%, particularly preferably at least 80%, most preferably at least 85%, at least 90%, at least 95%, and 100%, with the amino acid sequence shown in SEQ ID NO: 3, and also has alpha-glucosidase activity. Herein, the alpha-glucosidase activity means an enzyme activity of hydrolyzing starch from a non-reducing terminal and cutting D-glucose from it.

Examples of the FAT1 gene include a KJ strain-derived FAT1 gene (the nucleotide sequence of the gene: SEQ ID NO: 5, the nucleotide sequence of the mRNA: SEQ ID NO: 6, and the amino acid sequence: SEQ ID NO: 7) and a homologue thereof. A specific example of the FAT1 gene is a gene encoding a protein, which has an amino acid sequence having sequence identity of at least 50%, preferably at least 65%, particularly preferably at least 80%, most preferably at least 85%, at least 90%, at least 95%, and 100%, with the amino acid sequence shown in SEQ ID NO: 8 (i.e., a highly conserved amino acid sequence corresponding to an amino acid sequence at positions 78 to 283 in SEQ ID NO: 7), and also has acyl-ACP thioesterase activity. In addition, another specific example of the FAT1 gene is a gene encoding a protein, which has an amino acid sequence having sequence identity of at least 50%, preferably at least 65%, particularly preferably at least 80%, most preferably at least 85%, at least 90%, at least 95%, and 100%, with the amino acid sequence shown in SEQ ID NO: 7, and also has acyl-ACP thioesterase activity. Herein, the acyl-ACP thioesterase activity means an enzyme activity of hydrolyzing the thioester bond of acyl-ACP.

Examples of the DGAT2 gene include a KJ strain-derived DGAT2d gene (the nucleotide sequence of the gene: SEQ ID NO: 9, the nucleotide sequence of the mRNA: SEQ ID NO: 10, and the amino acid sequence: SEQ ID NO: 11) and a homologue thereof. A specific example of the DGAT2 gene is a gene encoding a protein, which has an amino acid sequence having sequence identity of at least 50%, preferably at least 65%, particularly preferably at least 80%, most preferably at least 85%, at least 90%, at least 95%, and 100%, with the amino acid sequence shown in SEQ ID NO: 12 (i.e., a highly conserved amino acid sequence corresponding to an amino acid sequence at positions 123 to 322 in SEQ ID NO: 11), and also has diacylglycerol acyltransferase activity. In addition, another specific example of the DGAT2 gene is a gene encoding a protein, which has an amino acid sequence having sequence identity of at least 50%, preferably at least 65%, particularly preferably at least 80%, most preferably at least 85%, at least 90%, at least 95%, and 100%, with the amino acid sequence shown in SEQ ID NO: 11, and also has diacylglycerol acyltransferase activity. Herein, the diacylglycerol acyltransferase activity means an enzyme activity of adding acyl-CoA-derived acyl group to diacylglycerol, so as to synthesize TAG.

The gene according to the present invention may be derived from, for example, strains belonging to the green algae as explained above, preferably strains belonging to the class Trebouxiophyceae, and particularly preferably strains belonging to genus *Coccomyxa* or genus *Pseudococcomyxa*.

Moreover, in the present invention, preferably, two, or all three of the AGL1 gene, the FAT1 gene and the DGAT2 gene are allowed to highly express.

There are many methods for allowing a protein encoded by the gene according to the present invention to highly express in cells of eukaryotic microalgae. The most common method is a method comprising constructing in vitro a construct comprising a promoter (a constitutively highly expressed promoter) ensuring the high expression of a gene(s) to be highly expressed, which is operably linked to the gene(s) to be highly expressed (for example, upstream of the gene(s)), and then introducing the construct into a host. Depending on purpose, a promoter having different strength and properties (constitutional or inducible) can be used.

After completion of transcription, an mRNA precursor is undergone posttranscriptional modification such as capping, splicing, or poly(A) addition, and is then transferred from the nucleus to the cytoplasm. An attempt to increase the efficiency of this posttranscriptional modification for the high expression of the gene(s) has not been made vigorously, in comparison to the use of promoters.

On the other hand, regarding the improvement of the translation efficiency of mRNA, there are multiple techniques. The efficiency of translation initiation is influenced by a sequence upstream of the start codon (5'-UTR) (Kim et al., 2014, Nucleic Acids Res, 42, 485). Thus, the translation efficiency can be improved by optimization of the 5'-UTR sequence. Moreover, a means for optimizing the codon usage of mRNA to achieve high expression has been broadly applied. That is to say, a codon-optimized gene is produced in vitro, and the produced gene is then introduced into a host, so that the amount of a protein translated can be increased.

As mentioned below, the gene according to the present invention of the KJ strain is induced by nitrogen deficiency, salt stress and the like. It is considered that this induction would be regulated by a transcriptional factor that positively or negatively regulates the expression of the gene. By identifying this transcriptional factor and elucidating the mechanism of the activation thereof the high expression of the gene according to the present invention can be achieved by utilizing the mechanism. In general, when a gene to be highly expressed is positively regulated by a certain transcriptional factor, the gene of interest can be highly expressed by allowing this transcriptional factor to highly express. On the other hand, when a gene to be highly expressed is negatively regulated by a certain transcriptional factor, the gene of interest can be highly expressed by losing the expression or activity of this negative transcriptional factor. Alternatively, even by operating a signaling system for activating or inactivating this transcriptional factor, the high expression of the gene of interest can be achieved.

In recent years, it has been gradually revealed that the expression of a gene can be positively or negatively regulated by a chromosome structure around the gene. Thus, the high expression of a gene to be highly expressed can be achieved by changing the chromosome structure around the gene, for example, by introduction of an insulator.

A specific example is a method for producing the genetically modified strain of eukaryotic microalgae according to the present invention by cloning the gene according to the present invention downstream of a strong promoter (e.g., a promoter for a KJ strain-derived EF1α gene (SEQ ID NO: 13)) and then introducing it into eukaryotic microalgae such as the KJ strain, as described in the Examples below.

Besides, as an example of the genetically modified strain of eukaryotic microalgae according to the present invention, a KJoxAFD-41417 strain, in which all of the three KJ strain-derived genes according to the present invention have been highly expressed in the KJ strain, which is shown in the following Examples, was deposited with the National Institute of Technology and Evaluation, Information on International Patent Organism Depositary (NITE-IPOD) (2-5-8-120, Kazusa Kamatari, Kisarazu-shi, Chiba-ken, Japan, postal code: 292-0818) under Accession No. FERM P-22294 on Aug. 27, 2015. Thereafter, this strain was further transferred to an international deposition under the provisions of the Budapest Treaty under Accession No. FERM BP-22294.

Furthermore, the present invention relates to a method for producing TAG by performing the mass culture of the above-described genetically modified strain of eukaryotic microalgae according to the present invention. As such a mass culture method, the previously established culture method described in Patent Literature 7, etc. can be applied. Specifically, this is a method of culturing microalgae using urea as a nitrogen source and also using a medium having a pH value of 4 or less. According to this culture method, a fluctuation in pH caused by nitrogen consumption can be reduced to minimum by using urea as a nitrogen source. In addition, since almost no bicarbonate ions are generated even if $CO_2$ is introduced into a culture medium with a pH value of 4 or less, this culture method is also characterized in that the pH of the culture medium is hardly fluctuated. Since the pH of the culture medium can be stably maintained at 4 or less according to this culture method, the proliferation of other microalgae or protists can be suppressed.

After completion of the culture, lipids including TAG can be obtained from the cultured product, for example, by hexane extract or the like.

EXAMPLES

Hereinafter, the present invention will be described in more detail in the following Examples. However, these Examples are not intended to limit the technical scope of the present invention.

In the following Examples, the AGL1 gene is a KJ strain-derived AGL1 gene (the nucleotide sequence of the gene: SEQ ID NO: 1, the nucleotide sequence of the mRNA: SEQ ID NO: 2, and the amino acid sequence: SEQ ID NO: 3), the FAT1 gene is a KJ strain-derived FAT1 gene (the nucleotide sequence of the gene: SEQ ID NO: 5, the nucleotide sequence of the mRNA: SEQ ID NO: 6, and the amino acid sequence: SEQ ID NO: 7), and the DGAT2 gene is a KJ strain-derived DGAT2d gene (the nucleotide sequence of the gene: SEQ ID NO: 9, the nucleotide sequence of the mRNA: SEQ ID NO: 10, and the amino acid sequence: SEQ ID NO: 11).

[Example 1] Analysis of Genes Associated with TAG Productivity According to RNA-Seq In the case of many microalgae, TAG production can be promoted under nitrogen deficiency conditions, or by adding approximately 100 mM NaCl to the medium under such nitrogen deficiency conditions. Also in the case of a KJ strain and a Pseudochoricystis ellipsoidea Obi strain that is closely related to the KJ strain (hereinafter referred to as an "Obi strain"; Satoh et al., 2010, J Jpn Inst Energ, 89, 909), an increase in the content of TAG was observed, when these strains were cultured under nitrogen deficiency conditions or were cultured with addition of NaCl. On the other hand, the amount of starch in each strain was reduced. The proliferation of cells and changes in the contents of TAG and starch in the KJ strain, which was cultured after addition of 100 mM NaCl, are shown in FIG. 1.

Specifically, the KJ strain was cultured in a culture medium, in which a medium (½ A6 medium) prepared by 2-fold diluting an A6 medium [2.5 mM $(NH_2)_2CO$, 378 µM $(NH_4)_2SO_4$, 405 µM $MgSO_4$, 265 µM $KH_2PO_4$, 264 µM $K_2HPO_4$, 61.2 µM $CaCl_2$, 1.20 µM $CuSO_4$, 1.13 µM $H_3BO_3$, 1.04 µM $ZnSO_4$, 0.622 µM $MnSO_4$, 0.294 µM $CoCl_2$, 12.4 nM $Na_2MoO_4$, and 0.4% (v/v) Fe solution (3 g/L citric acid, 4.9 g/L ammonium ferric citrate, and 0.5 g/L EDTA-2Na)] with sterilized water was used, until it resulted in $OD_{750}=3$. Thereafter, 0 or 100 mM NaCl was added to the culture, and the sample 0 hour, 24 hours, and 72 hours after the addition of NaCl, was measured in terms of cell dry weight (g/L), TAG weight per cell dry weight, and starch weight (% DW) per cell dry weight. In FIG. 1, the filled bar indicates the results with no addition of NaCl, and the open bar indicates the results with addition of 100 mM NaCl. The content of oil was measured using NMR under the following conditions. That is, the cells were harvested by centrifugation at 8,000 rpm for 5 minutes or more, and were then freeze-dried. Thereafter, approximately 40 mg of cells was weighed, and the oil content per unit cell dry weight was measured using the oil measurement device MQC, manufactured by Oxford Instruments. A calibration curve was produced using the olive oil of Japanese Pharmacopoeia as a standard substance.

As shown in FIG. 1, the proliferation of cells was slightly promoted by addition of NaCl. On the other hand, the TAG content was significantly increased, and the starch content was significantly decreased.

Moreover, utilizing the database of plant metabolic pathway (http://www.plantcyc.org/), the amino acid sequences of enzymes associated with lipid metabolism or starch metabolism were obtained. Using these amino acid sequences as queries, Tblastn searching was performed on the genomic sequences of the KJ strain or the Obi strain, or on the mRNA sequences obtained by transcriptome analysis (RNA-seq), so that the amino acid sequences of enzymes associated with the lipid metabolism or starch metabolism of the KJ strain and the Obi strain, and the genes thereof were identified. Furthermore, the expression levels of the genes and changes in the expression levels were analyzed by using the results of the RNA-seq.

As a result, it was found that the expression of the alpha-glucosidase (AGL1) gene associated with the decomposition of starch was strongly induced both in the KJ strain and in the Obi strain by addition of NaCl. In addition, it was also found that the expression of the acyl-ACP thioesterase (FAT1) gene acting at the final stage of fatty acid synthesis, and the expression of the DGAT2d gene that is one of polymeric genes of diacylglycerol acyltransferase (DGAT) acting at the final stage of the Kennedy pathway for TAG synthesis, were also induced strongly by addition of NaCl.

Figure 2:
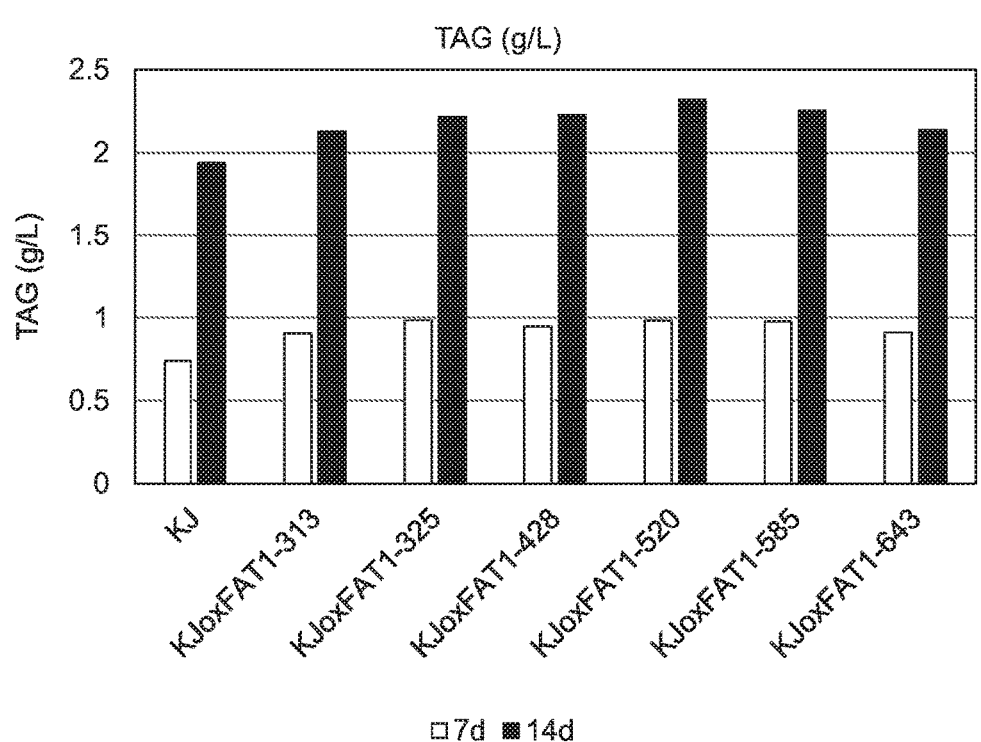
FIG. 2 includes graphs showing the influence of NaCl on the expression of the AGL1 gene, FAT1 gene, and DGAT2d gene in the KJ strain.

FIG. 2 shows the expression of the AGL1, FAT1, and DGAT2d genes in the KJ strain upon addition of 0 and 100 mM NaCl. Specifically, as with FIG. 1, the KJ strain was cultured in a culture medium, in which the ½ A6 medium was used, until it resulted in $OD_{750}=3$, and the expression levels of the genes in the sample 0 hour, 24 hours, and 48 hours after addition of 0 or 100 mM NaCl were analyzed by RNA-seq. In FIG. 2, the longitudinal axis of the graph indicates FPKM (Fragments Per Kilobase of transcript per Million mapped reads). The expression of the FAT1 gene, DGAT2d gene, and AGL1 gene was increased even without addition of NaCl, as the culture time elapsed. However, in the case of addition of NaCl, the expression levels were further increased. It is considered that an increase in the gene expression under conditions without addition of NaCl would be probably caused by a reduction in the nitrogen concentration in the medium.

Figure 3:
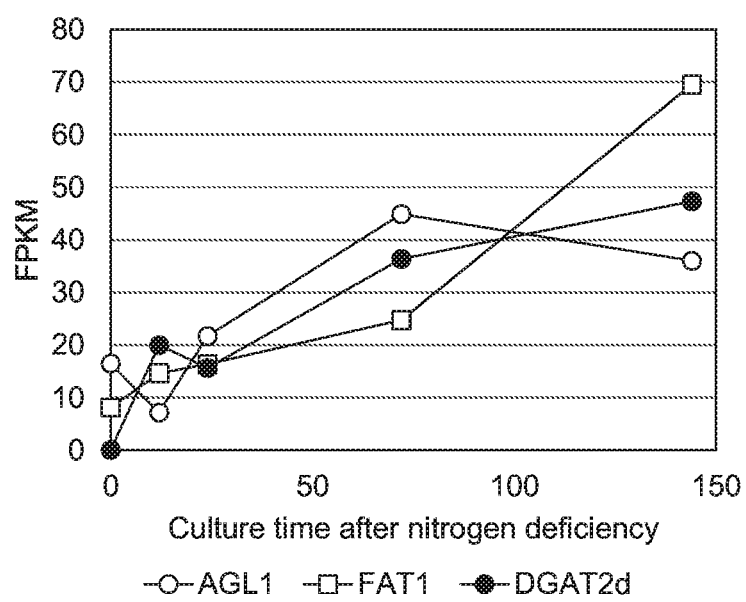
FIG. 3 is a graph showing the influence of nitrogen deficiency conditions on the expression of the AGL1 gene, FAT1 gene, and DGAT2d gene in the KJ strain.

Moreover, these genes were also induced under nitrogen deficiency conditions (FIG. 3). Specifically, the KJ strain was cultured in a nitrogen-sufficient medium (MA5), and was then transferred into a nitrogen-deficient medium (MA5-N). Thereafter, 12, 24, 72, and 144 hours after the transfer, sampling was carried out, and the expression levels of the genes in the sample were examined by RNA-seq. In FIG. 3, the longitudinal axis of the graph indicates the mean value (N=2) of FPKM (Fragments Per Kilobase of transcript per Million mapped reads). The medium MA5 consisted of 18 mM $NaNO_3$, 0.4 mM $MgSO_4$, 60 µM $CaCl_2$, 0.26 mM $KH_2PO_4$, 0.26 mM $K_2HPO_4$, 20 mM HEPES-KOH (pH 7.0), 0.4% (v/v) Fe solution, and 0.1% (v/v) trace elements. With regard to the composition of a stock solution used to prepare this medium, the Fe solution consisted of 3 g/L citric acid, 4.9 g/L ammonium iron citrate, and 0.5 g/L EDTA, and the trace elements consisted of 70 mg/L $H_3BO_3$, 150 mg/L $MnSO_4 \cdot 5H_2O$, 300 mg/L $ZnSO_4 \cdot 7H_2O$, 300 mg/L $CuSO_4 \cdot 5H_2O$, 70 mg/L $CoCl_2 \cdot 6H_2O$, and 3 mg/L $Na_2MoO_4$. In the case of MA5-N, $NaNO_3$ was not used, and NaCl was added to the medium to have the same concentration of $Na^+$.

These genes encode enzymes acting at the final stage of fatty acid synthesis, TAG synthesis, and starch decomposition, respectively. Thus, the present inventors have considered that a strain having more improved TAG productivity could be obtained by highly expressing these genes, and have attempted to produce such a high expression strain.

[Example 2] Production of Strains Highly Expressing cDNAs of AGL1 Gene, FAT1 Gene, and DGAT2d Gene In order to allow the cDNAs of the AGL1 gene, FAT1 gene, and DGAT2d gene to highly express in the KJ strain, alone or simultaneously in plural forms, the promoter (SEQ ID NO: 13) and terminator (SEQ ID NO: 14) of a gene encoding EF1α that is an α subunit of a translation elongation factor of the KJ strain (hereinafter referred to as "KJEF1A") were utilized. The cDNA of each of the AGL1 gene, FAT1 gene and DGAT2d gene was inserted between the promoter and the terminator of KJEF1A to produce pAGL1, pFAT1 and pDGAT2d plasmids, respectively (FIG. 4).

Figure 4:
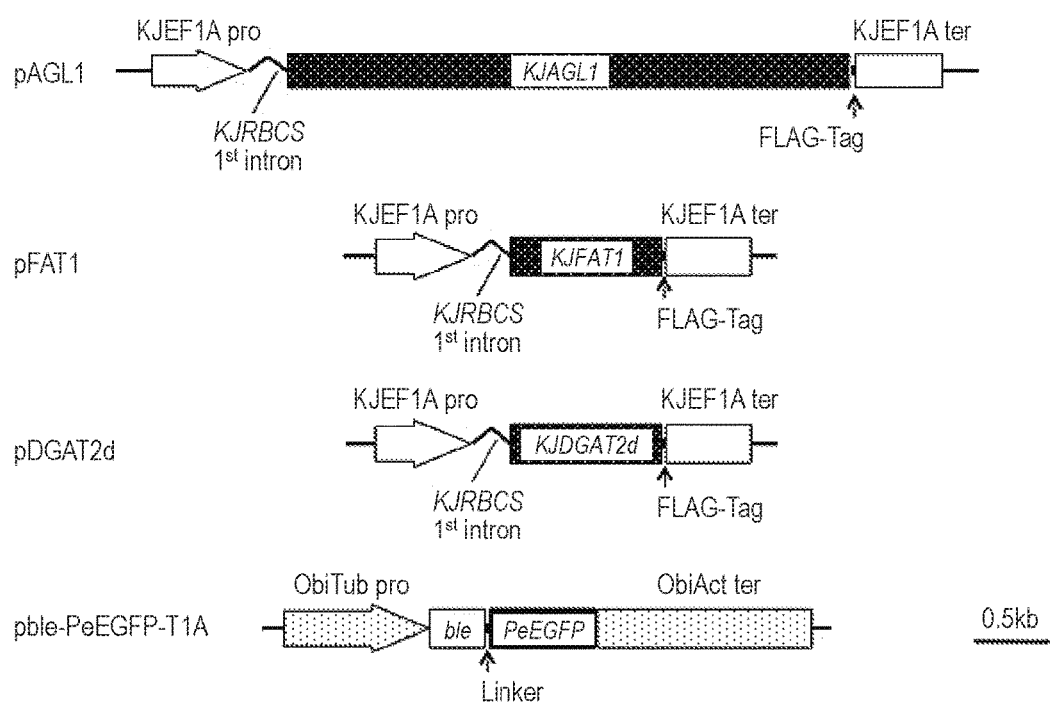
FIG. 4 is a schematic view showing the structures of pAGL1, pFAT1, pDGAT2d, and pble-PeEGFP-T1A plasmids.

In FIG. 4, KJEF1A pro and KJEF1A ter indicate sequences comprising the promoter and terminator of the EF1A gene (KJEF1A) of the KJ strain, respectively. KJRBCS indicates a RuBisCO small subunit gene of the KJ strain, and the initial intron sequence thereof (SEQ ID NO: 15) is inserted between the promoter and cDNA. The central portion of each plasmid indicates the cDNA sequence of each gene. FLAG-Tag is a DNA fragment encoding a peptide sequence that is N-terminus-DYKDDDDK-C-terminus. ObiTub pro and ObiAct ter are sequences comprising the Tubulin gene promoter and the Actin gene terminator of the Obi strain, respectively (Imamura et al., 2012, J Gen Appl Microbiol, 58, 1). The term "ble" indicates a bleomycin- or zeomycin [brand name: Zeocin™]-resistant gene (Stevens et al., 1996, Mol. Gen. Genet. 251, 23-30.). Linker indicates a DNA fragment encoding a peptide sequence that is N-terminus-GGSGGR-C terminus. PeEGFP indicates a sequence prepared by optimizing the codon usage of EGFP (enhanced GFP; highly sensitive GFP) for the expression in the Obi strain.

These plasmids, together with a pG418-T1A plasmid for imparting G418 resistance (Kasai et al., 2015, Biotechnol Biofuels, 8, 94), were co-introduced into the KJ strain according to particle bombardment, and G418-resistant colonies were then selected.

In an experiment regarding introduction of the pAGL1 plasmid, the total length of a portion between the 5'-terminus of the KJEF1A promoter and the 3'-terminus of the KJEF1A terminator of the pAGL1 plasmid shown in FIG. 4 (hereinafter referred to as a "KJAGL1 cDNA expression cassette") was inserted into 6 strains (5.7%) out of 106 G418-resistant colonies. In an experiment regarding introduction of the pFAT1 plasmid, the total length of the KJFAT1 cDNA expression cassette was inserted into 18 strains (5.0%) out of 365 G418-resistant colonies. In an experiment regarding introduction of the pDGAT2d plasmid, insertion of the total length of the KJDGAT2d cDNA expression cassette into 6 strains (3.7%) out of 164 G418-resistant colonies could be confirmed.

Figure 5:
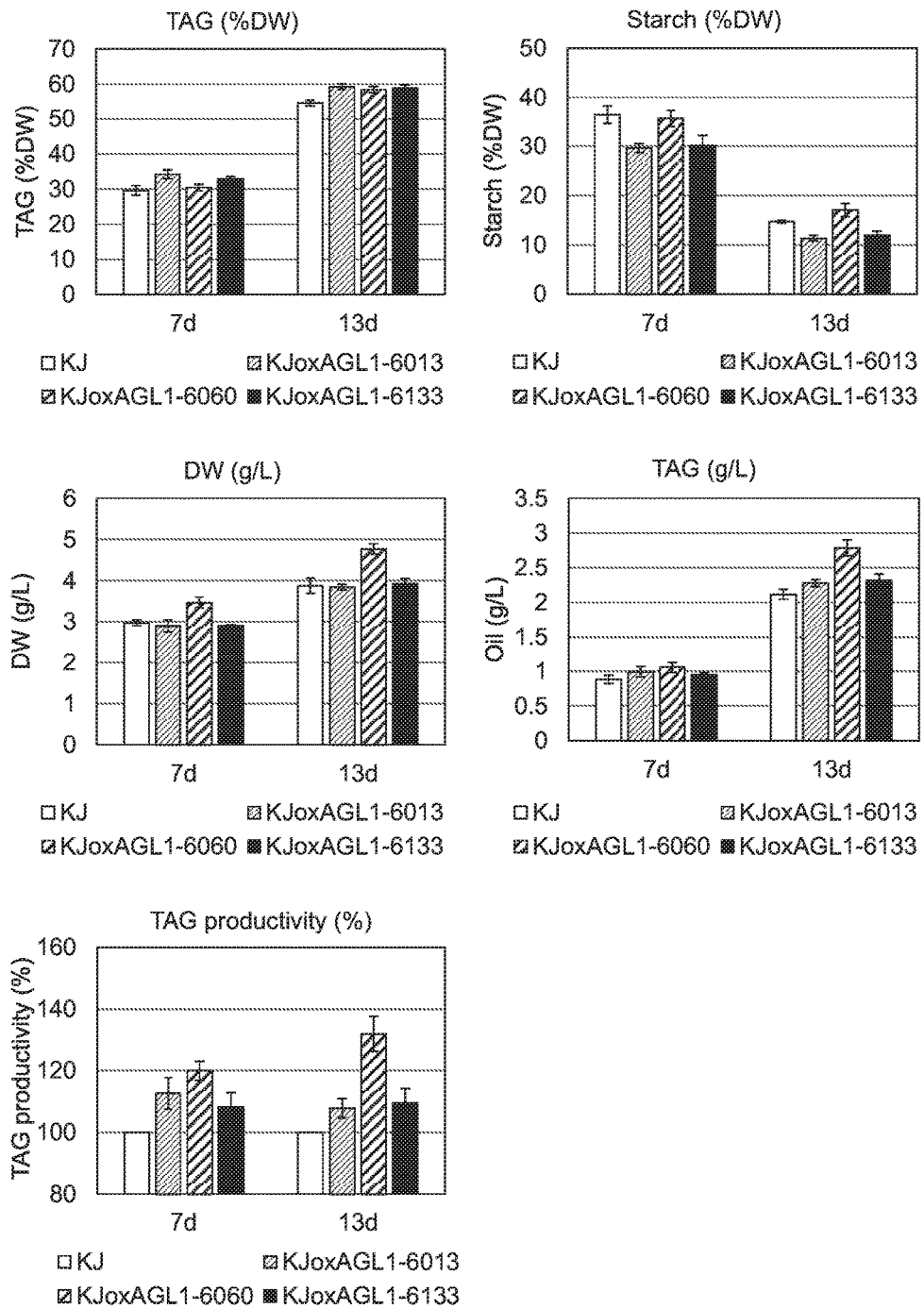
FIG. 5 includes graphs showing the TAG content (% DW) per cell dry weight (DW), the starch content (% DW) per cell dry weight (DW), the cell dry weight (g/L), the TAG production amount (g/L) per culture medium and the TAG productivity (%), of the KJ strain and three pAGL1 plasmid-transformed strains (KJoxAGL1-6013, 6060, and 6133).

[Example 3] Evaluation of TAG Productivity of KJAGL1 cDNA High Expression Strains The expression of KJAGL1 cDNA in the 6 transformed strains obtained by introduction of the pAGL1 plasmid was analyzed by Real time PCR. In the case of a KJoxAGL1-6060 strain (wherein "ox" indicates overexpression line; high expression strain) in which the expression of KJAGL1 cDNA was highest, the TAG productivity on Day 13 of the culture was approximately 1.3 times higher than the TAG productivity of a wild-type strain (FIG. 5). In the case of the remaining strains, the TAG content was slightly increased and the starch content was slightly decreased, but the TAG productivity was almost equivalent to that of the wild-type strain.

Herein, the term "TAG productivity" means the TAG production amount (%) of a transformed strain when the TAG production amount (g/L) of a wild-type strain (KJ) is set at 100%. In the present Example, individual strains were simultaneously cultured in a ½ DENSO medium, and then, sampling was carried out on Day 7 (7d) and Day 13 (13d). In FIG. 5, the bar graph and the error bar indicate the mean value and standard error (n=3) of the samples obtained from three independent experiments, respectively. Besides, the DENSO medium had almost the same composition as the A6 medium, but the concentrations of $(NH_4)_2SO_4$ and $(NH_2)_2CO$ were 863 μM and 2.38 mM, respectively. The ½ DENSO medium was obtained by 2-fold diluting the DENSO medium with distilled water.

Figure 6:
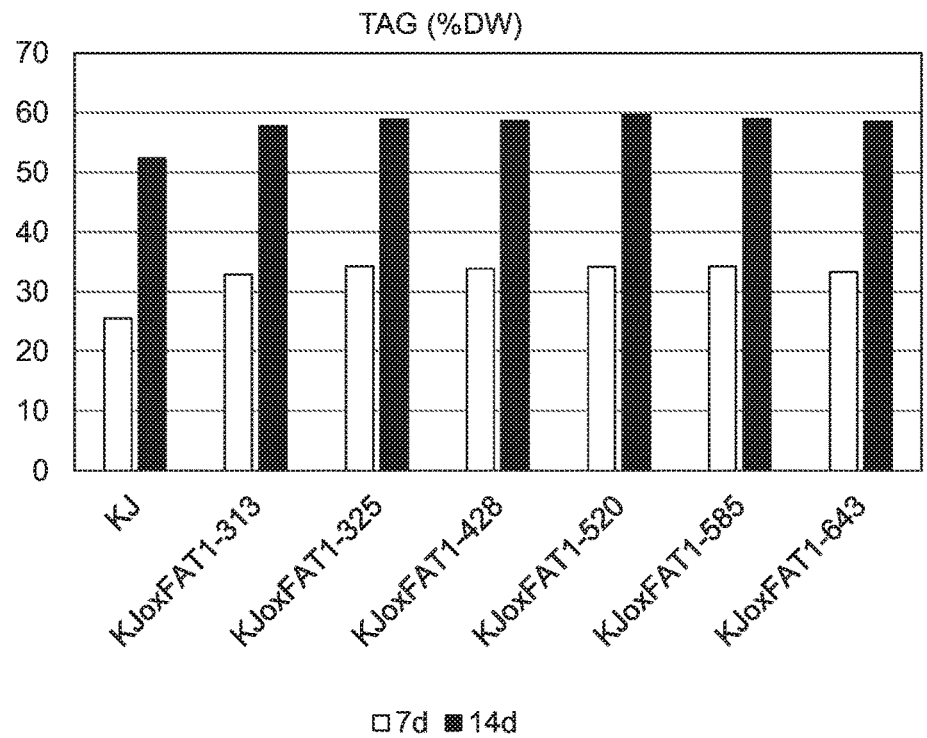
Figure 1:
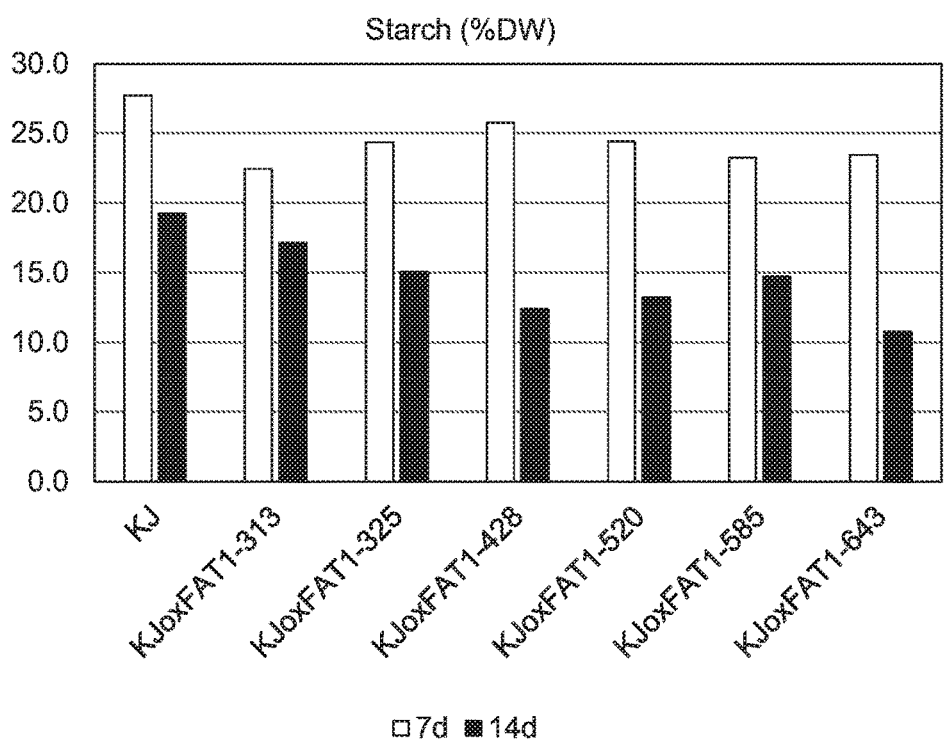
Figure 6:
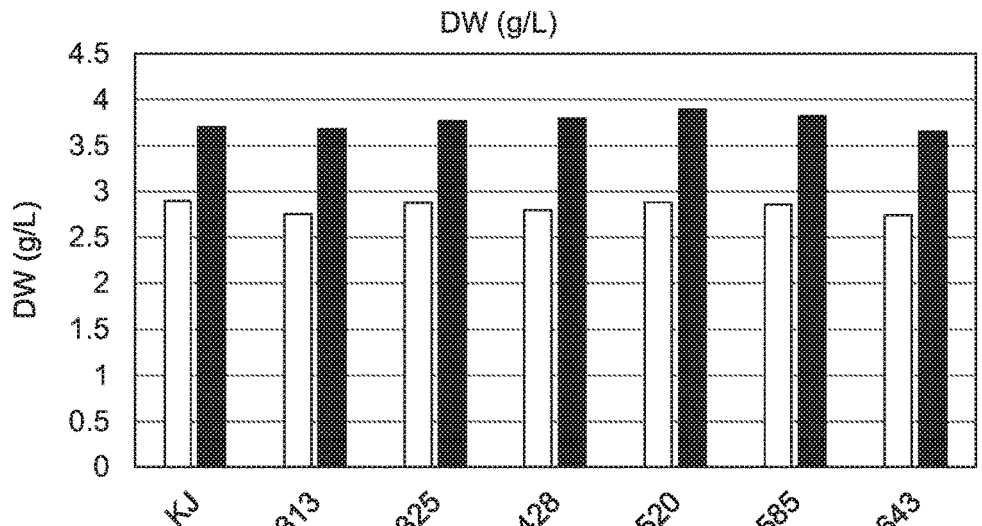

[Example 4] Evaluation of TAG Productivity of KJFAT1 cDNA High Expression Strains The TAG productivity of the 18 transformed strains obtained by introduction of the pFAT1 plasmid was evaluated. In 12 out of the 18 strains, the TAG content rate was increased. In 6 out of the 12 strains, in which a reduction in the cell dry weight was not significantly observed (i.e., proliferation was not deteriorated), the TAG productivity was increased approximately 1.2 to 1.3 times on Day 7 of the culture, and was then increased approximately 1.1 to 1.2 times on Day 14 of the culture (FIG. 6). At this time, a decrease in the starch content was observed at the same time of an increase in the TAG content. Accordingly, it was considered that an increase in the TAG content by introduction of the pFAT1 plasmid would be attended with a decrease in the starch content (FIG. 6). In the present Example, individual strains were simultaneously cultured in a ½ DENSO medium, and then, sampling was carried out on Day 7 (7d) and Day 14 (14d).

Figure 7:
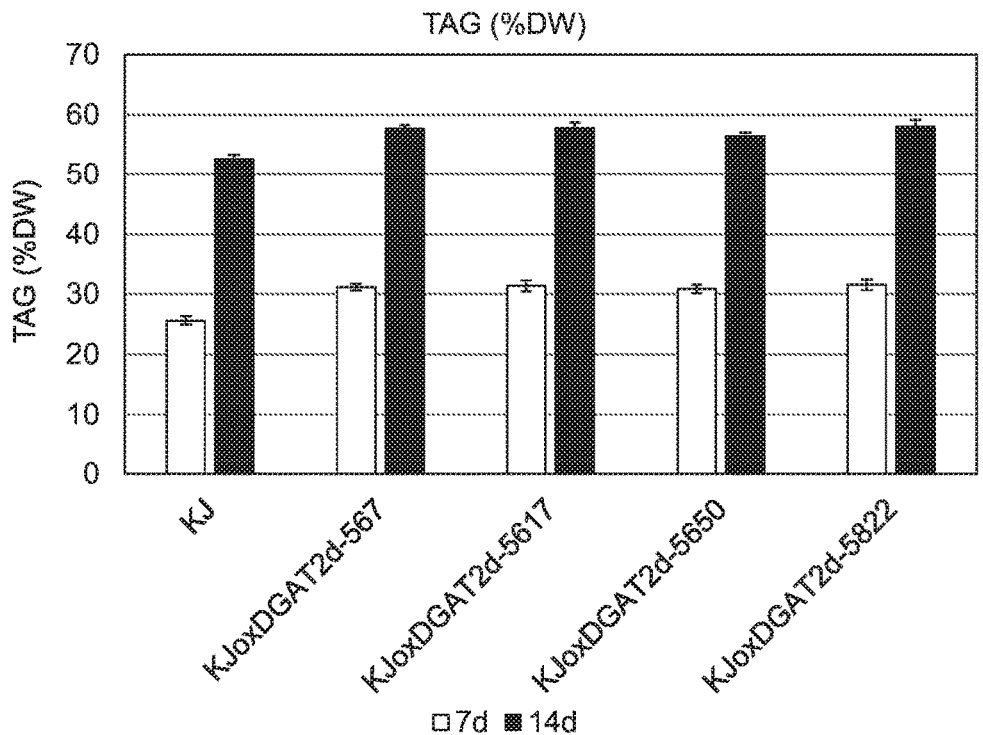
Figure 1:
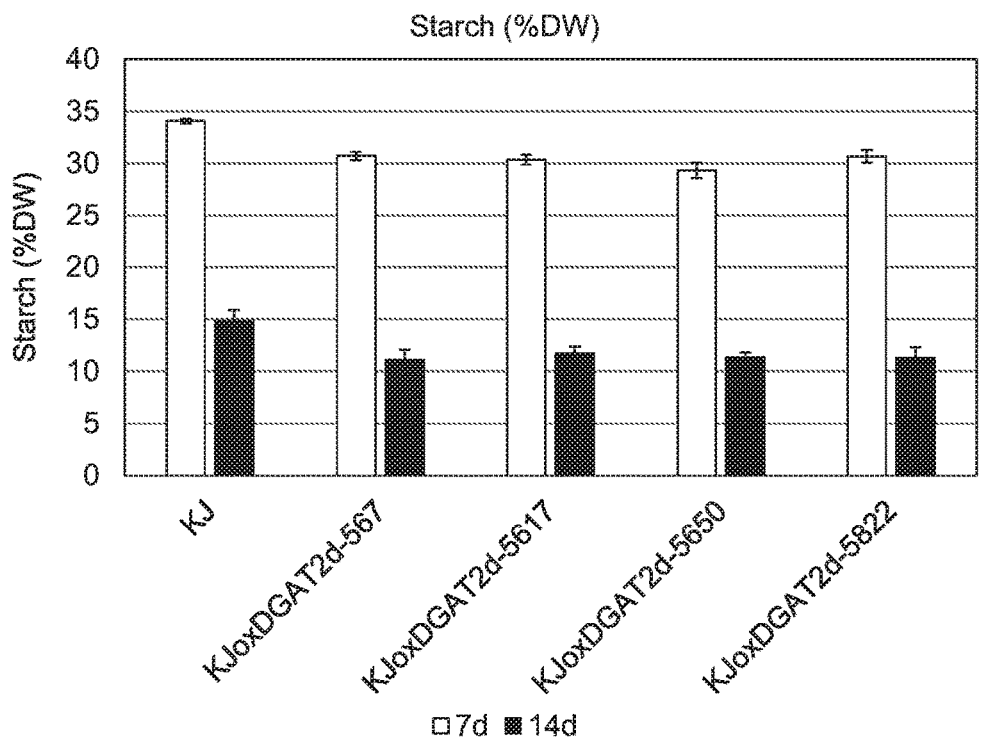
Figure 7:
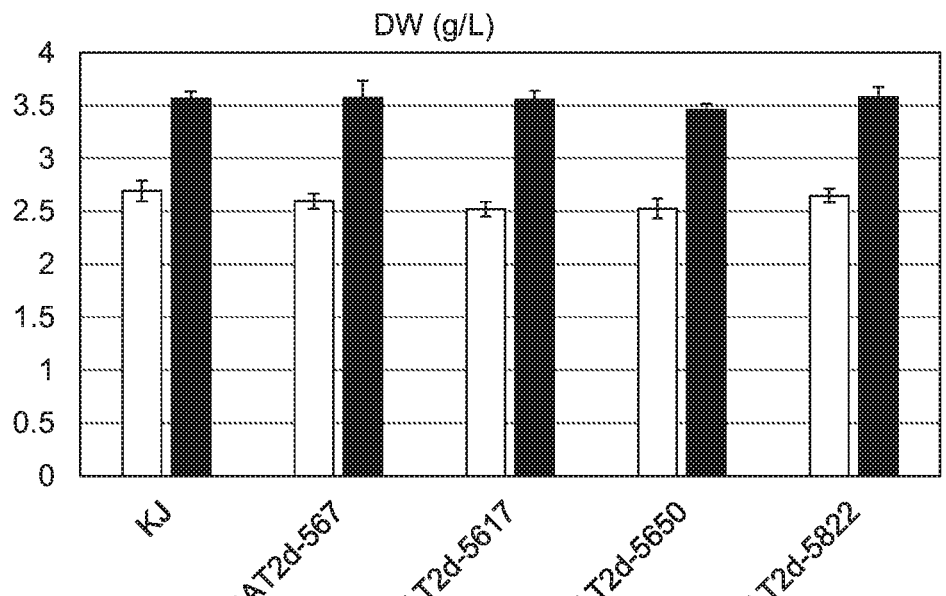
Figure 2:
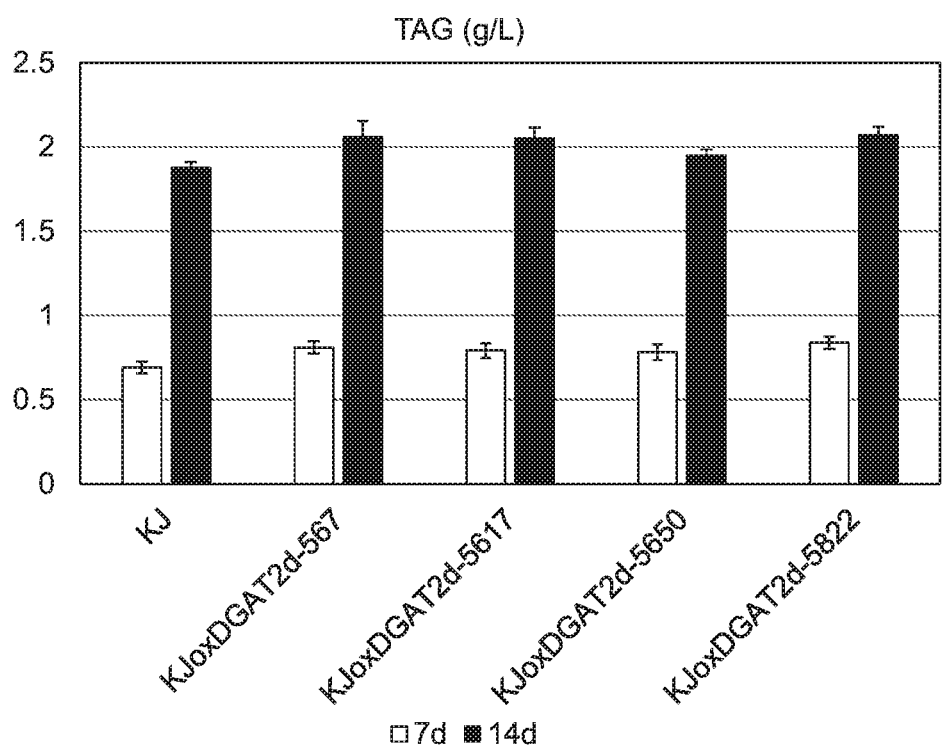
Figures 3, 7:
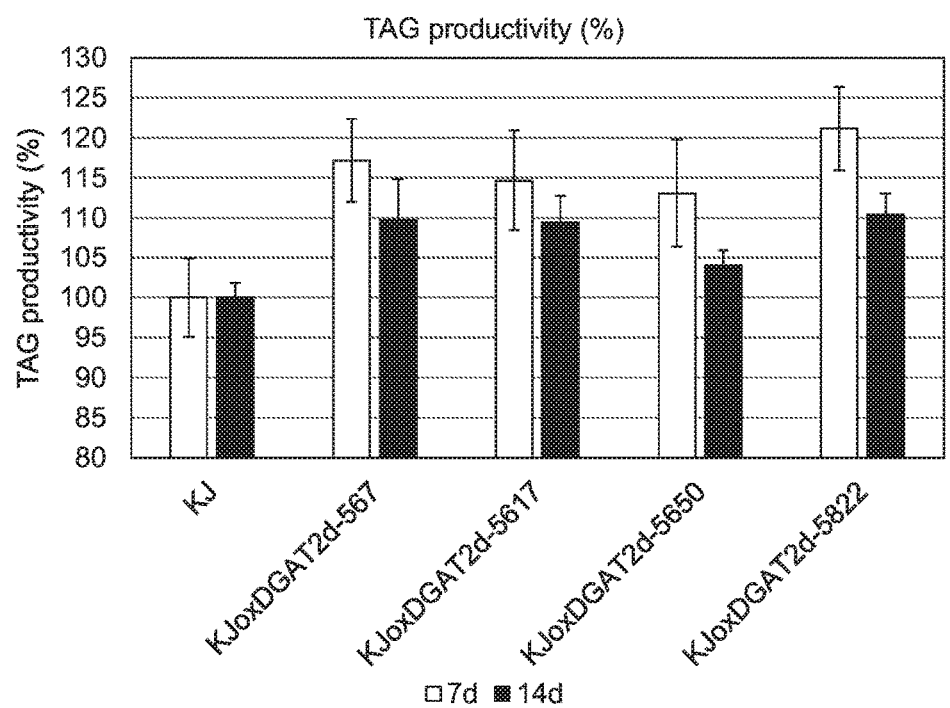

[Example 5] Evaluation of TAG Productivity of KJDGAT2d cDNA High Expression Strains In 4 out of the 6 transformed strains obtained by introduction of the pDGAT2d plasmid (KJoxDGAT2d-567, 5617, 5650, and 5822), a significant increase in the TAG content rate per cell dry weight was observed ($P<0.01$, Student's t-test). On Day 7 of the culture, the TAG content rate was increased approximately 1.2 times, and was then increased approximately 1.1 times that of a wild-type strain on Day 14 of the culture (FIG. 7). At this time, the starch content rate was decreased in 4 strains in which an increase in TAG was observed ($P<0.05$, Student's t-test). Accordingly, it was considered that an increase in the TAG content rate caused by the high expression of KJDGAT2d cDNA would be attended with a decrease in the starch content rate (FIG. 7). In the present Example, individual strains were simultaneously cultured in a ½ DENSO medium, and then, sampling was carried out on Day 7 (7d) and Day 14 (14d). In FIG. 7, the bar graph and the error bar indicate the mean value and standard error (n=3 to 6) of the samples obtained from independent experiments, respectively.

[Example 6] Production of Strain in which Multiple cDNAs are Simultaneously Highly Expressed Into a KJoxFAT1-325 strain (FIG. 6) having the highest TAG productivity on Day 7, among the pFAT1 plasmid-transformed strains, a pDGAT2d plasmid and a pble-PeEGFP-T1A plasmid were co-introduced, and thereafter, 228 Zeo-resistant colonies were selected. Insertion of the KJDGAT2d cDNA expression cassette was analyzed by PCR and as a result, it could be confirmed that the total length of the KJDGAT2d cDNA expression cassette was inserted in 13 strains (5.7%).

In order to analyze the degree of improved TAG productivity when multiple cDNAs are simultaneously allowed to highly express in a single cell, four transformed strains in which the cDNAs of three genes were combined with one another (AGL1 & FAT1, AGL1 & DGAT2d, FAT1 & DGAT2d, and AGL1 & FAT1 & DGAT2d) were produced. A pFAT1 plasmid and a pble-PeEGFP-TIA plasmid were co-introduced into a KJoxAGL1-6060 strain having the highest TAG productivity among the pAGL1 plasmid-transformed strains, and thereafter, 237 zeocin (Zeo)-resistant colonies were selected. It was confirmed that the total length of the KJFAT1 cDNA expression cassette was inserted in 17 strains (7.2%). Likewise, a pDGAT2d plasmid and a pble-PeEGFP-T1A plasmid were co-introduced into the KJox-AGL1-6060 strain, and thereafter, 130 Zeo-resistant colonies were selected. It was confirmed that the total length of the DGAT2d cDNA expression cassette was inserted in 18 strains (13.8%).

In order to allow the cDNAs of three genes to highly express in a single cell, three plasmids, namely, pFAT1, pDGAT2d and pble-PeEGFP-T1A were simultaneously introduced into the KJoxAGL1-6060 strain, and thereafter, 685 Zeo-resistant colonies were selected. Among these strains, both a KJFAT1 cDNA expression cassette and a KJDGAT2d cDNA expression cassette were inserted in 17 strains (2.5%).

[Example 7] Evaluation of TAG Productivity of Strain in which Multiple cDNAs are Highly Expressed As described in Example 6, among the KJoxFAT1-325 strains (FIG. 6) into which the KJDGAT2d cDNA expression cassette had been introduced, namely, among 13 strains in which the KJFAT1 cDNA and the KJDGAT2d cDNA had been highly expressed, a KJoxFD-2643 strain having the highest TAG productivity was analyzed in detail. In addition, the procedures for constructing transformed strains are shown below.

KJ→(+KJDGAT2d cDNA)→KJoxDGAT2d-5822
KJ→(+KJFAT1 cDNA)→KJoxFAT1-325
KJoxFAT1-325→(+KJDGAT2d cDNA)→KJoxFD-2643
KJ→(+KJAGL1 cDNA)→KJoxAGL1-6060
KJoxAGL1-6060→(+KJFAT1 cDNA)→(17 strains)
KJoxAGL1-6060→(+KJDGAT2d cDNA)→(18 strains)
KJoxAGL1-6060→(+KJFAT1 cDNA+KJDGAT2d cDNA)→KJoxAFD-41417

In the above construction procedures, the names of strains, which were constructed by introducing the cDNA expression cassette in the parentheses into a KJ strain, are shown. A KJDGAT2d cDNA expression cassette was introduced again into the KJoxFAT1-325 strain to produce a KJoxFD-2643 strain. The names of strains produced by introducing only the KJFAT1 cDNA expression cassette or only the KJDGAT2d cDNA expression cassette into a KJoxAGL1-6060 strain are not shown herein. A KJFAT1 cDNA expression cassette and a KJDGAT2d cDNA expression cassette were simultaneously introduced into the KJoxAGL1-6060 strain to produce a KJoxAFD-41417 strain.

Figure 8:
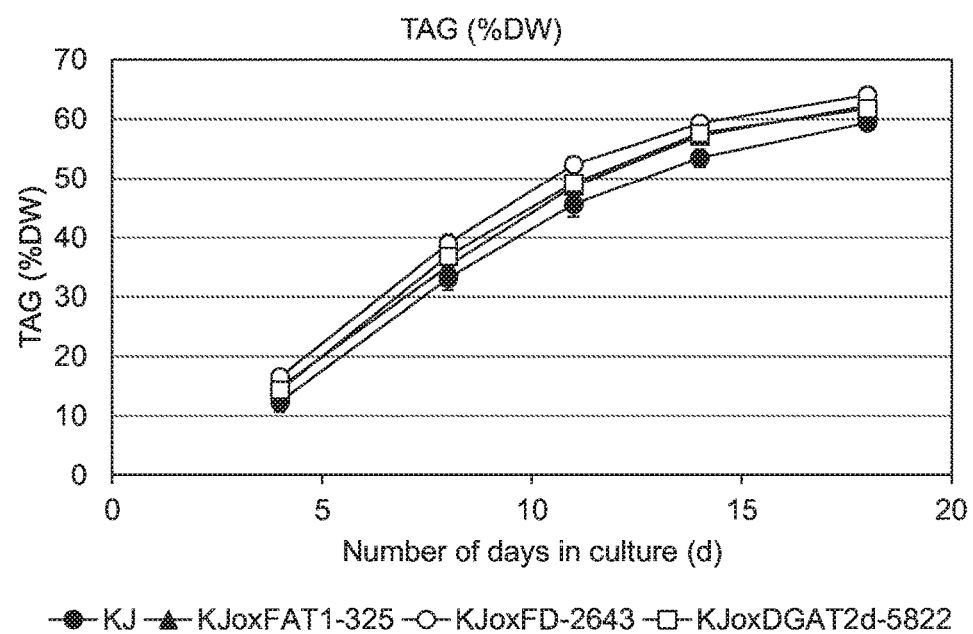
FIG. 8 is a graph showing the mean value and standard error (n=3) of the TAG content (% DW) per cell dry weight of each of the KJ strain, the KJoxDGAT2d-5822 strain prepared by introducing a KJDGAT2d cDNA expression cassette into the KJ strain, the KJoxFAT1-325 strain prepared by introducing a KJFAT1 cDNA expression cassette into the KJ strain, and the KJoxFD-2643 strain prepared by introducing a KJDGAT2d cDNA expression cassette into a KJoxFAT1-325 strain.

The KJ strain, KJoxFAT1-325 strain, KJoxDGAT2d-5822, and KJoxFD-2643 strain were each adjusted with a ½ DENSO medium to initial $O.D._{750}=0.2$, and thereafter, the culture was initiated. From Day 4 to Day 18 of the culture, the TAG content rate (% DW) per cell dry weight was measured. As a result, the TAG content rate was increased in the KJoxFAT1-325 strain and the KJoxDGAT2d-5822 strain, rather than in the wild-type strain. However, the TAG content rate in the KJoxFD-2643 strain was further increased, rather than in those strains (FIG. 8). Specifically, the high expression of FAT1 and DGAT2d additively increased the TAG content rate in the KJ strains. Individual strains were simultaneously cultured in a ½ DENSO medium, and then, sampling was carried out on Days 4, 8, 11, 14, and 18 of the culture.

In addition, the TAG productivity of the KJoxAGL1-6060 strain that is a KJAGL1 cDNA expression cassette-introduced strain was approximately 30% higher than that of a wild-type strain (FIG. 5). Seventeen KJoxAGL1-6060 strains, into which only the KJFAT1 cDNA expression cassette had been introduced, and also, eighteen 18 KJoxAGL1-6060 strains, into which only the KJDGAT2d cDNA expression cassette had been introduced, were separated, and thereafter, the TAG productivity of these strains was examined. As a result, among these expression cassette-introduced strains, there were found no strains exhibiting TAG productivity that was significantly higher than that of the KJoxAGL1-6060 strain as a parent strain.

On the other hand, a KJoxAFD-41417 strain, which had been prepared by simultaneously introducing the KJFAT1 cDNA expression cassette and the KJDGAT2d cDNA expression cassette into the KJoxAGL1-6060 strain, exhibited much higher TAG productivity than that of the parent strain, as described below.

Figure 9:
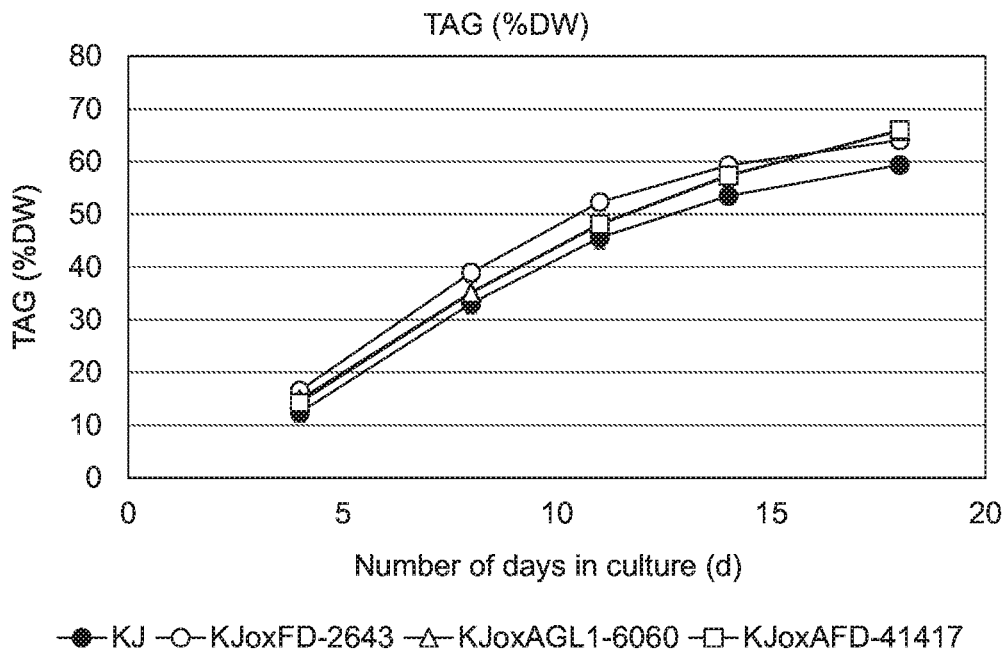
Figure 1:
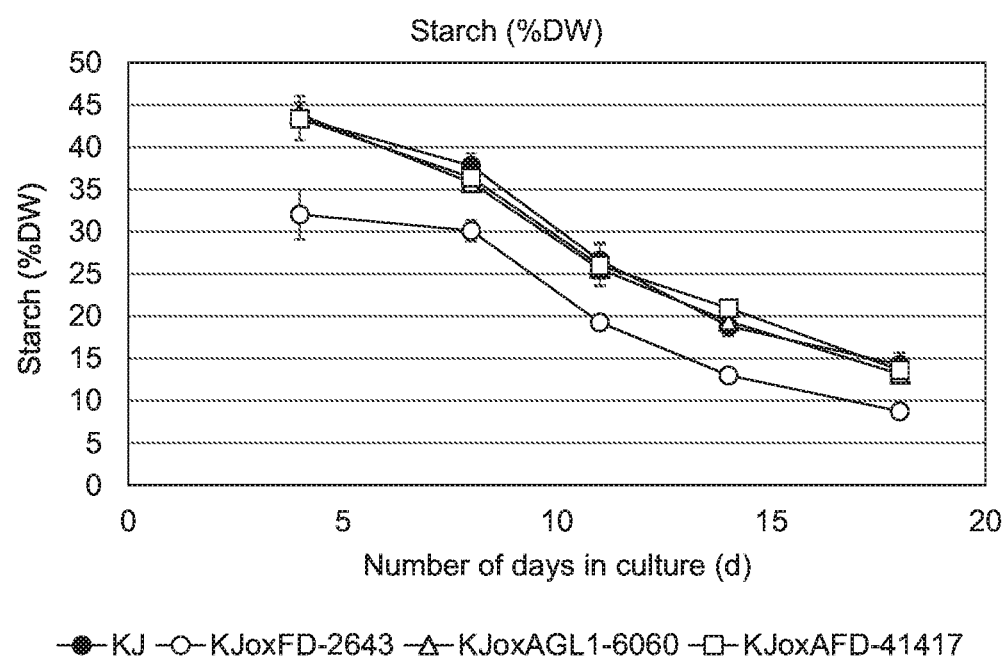
Figure 9:
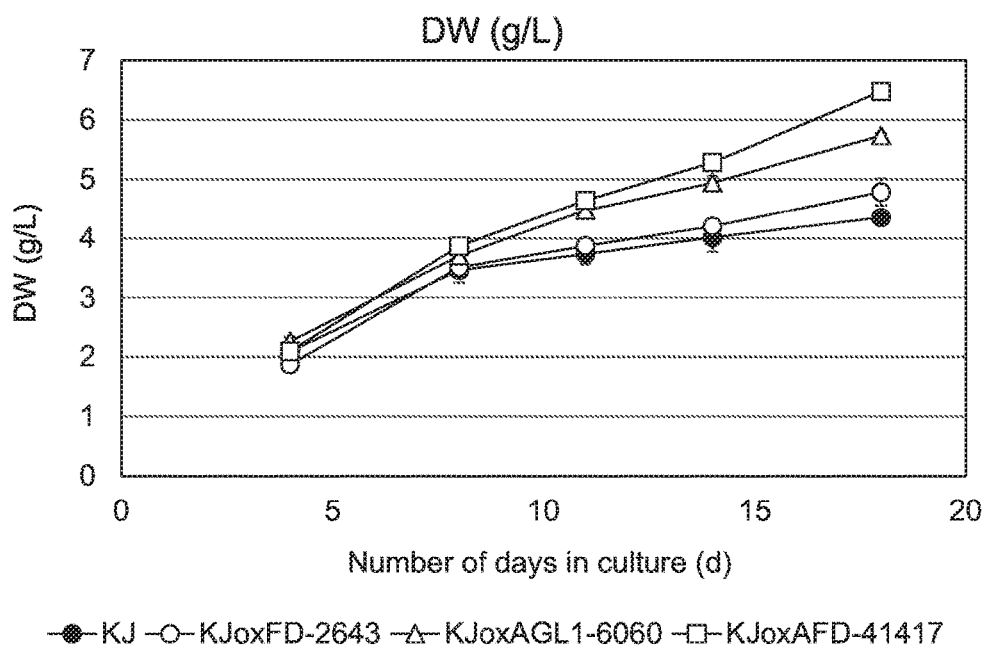
Figure 2:
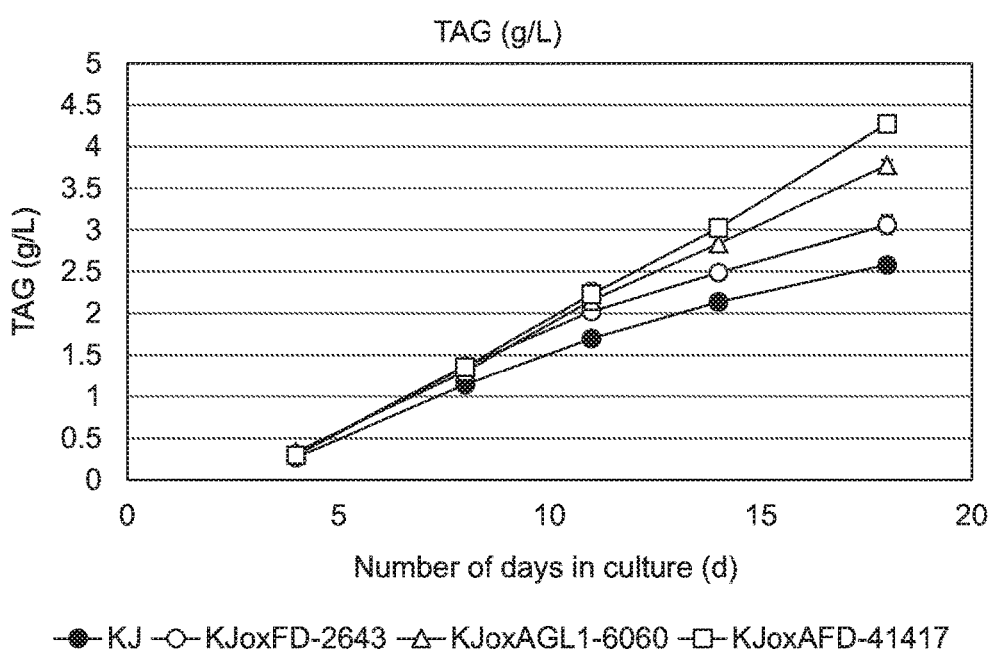
Figures 3, 9:
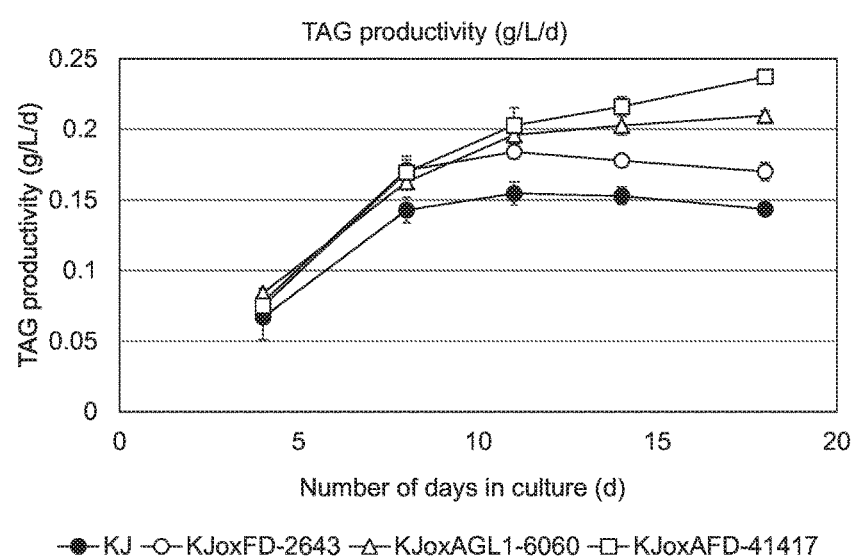

The KJ strain, and the aforementioned KJoxFD-2643 strain (a KJFAT1 cDNA expression cassette+KJDGAT2d expression cassette-introduced strain), KJAGL1 cDNA expression cassette-introduced strain (KJoxAGL1-6060) and KJoxAFD-41417 strain were adjusted with a ½ DENSO medium to initial $O.D._{750}=0.2$, and the culture was then initiated. From Day 4 to Day 18 of the culture, the TAG production amount (g/L) per culture medium was measured. In the KJoxFD-2643 strain, the TAG production amount (g/L) on Day 18 of the culture was increased approximately 1.2 times that of the wild-type strain, whereas in the KJoxAGL1-6060 strain, it was increased approximately 1.5 times that of the wild-type strain. On the other hand, in the KJoxAFD-41417 strain, the TAG production amount (g/L) on Day 18 of the culture was increased approximately 1.7 times that of the wild-type strain (FIG. 9). Moreover, the TAG productivity (g/L/d) became maximum from Day 8 to Day 14 of the culture in the wild-type strain and the KJoxFD-2643 strain, whereas in the KJoxAGL1-6060 strain and the KJoxAFD-41417 strain having the KJoxAGL1-6060 strain as a parent strain, the TAG productivity was increased up to Day 18 of the culture (FIG. 9). Individual strains were simultaneously cultured in a ½ DENSO medium, and then, sampling was carried out on Days 4, 8, 11, 14, and 18 of the culture.

From the aforementioned results, it was demonstrated that TAG productivity was additively increased by the high expression of KJDGAT2d cDNA and the high expression of KJFAT1 cDNA, and also that a strain having TAG productivity that is approximately 1.7 times higher than that of a wild-type strain can be produced by combining the high expression of KJAGL1 cDNA with the high expression of the above two cDNAs.

Accession Numbers
FERM BP-22254
FERM BP-22294

All publications, patents and patent applications cited in the present description are incorporated herein by reference in their entirety.

The invention claimed is:

1. A genetically modified strain of eukaryotic microalgae, in which a gene encoding an alpha-glucosidase (AGL1) protein is highly expressed, wherein
   triacylglycerol (TAG) productivity is improved in comparison to a parent strain thereof, and
   the AGL1 protein has an amino acid sequence having sequence identity of at least 90% with the amino acid sequence shown in SEQ ID NO: 4, and has alpha-glucosidase activity.

2. The genetically modified strain of eukaryotic microalgae according to claim 1, in which a gene encoding an acyl-ACP thioesterase (FAT1) protein and/or a gene encoding a diacylglycerol acyltransferase 2 (DGAT2) protein are also highly expressed, wherein
   the FAT1 protein has an amino acid sequence having sequence identity of at least 90% with the amino acid sequence shown in SEQ ID NO: 8, and has acyl-ACP thioesterase activity, and the DGAT2 protein has an amino acid sequence having sequence identity of at least 90% with the amino acid sequence shown in SEQ ID NO: 12, and has diacylglycerol acyltransferase activity.

3. The genetically modified strain of eukaryotic microalgae according to claim 1, wherein the genes are operably linked to a promoter ensuring the high expression of the genes.

4. The genetically modified strain of eukaryotic microalgae according claim 1, which belongs to the class Trebouxiophyceae.

5. The genetically modified strain of eukaryotic microalgae according to claim 4, which belongs to genus *Coccomyxa* or genus *Pseudococcomyxa*.

6. The genetically modified strain of eukaryotic microalgae according to claim 1, wherein the genes are derived from a strain belonging to green algae.

7. The genetically modified strain of eukaryotic microalgae according to claim 6, wherein the genes are derived from a strain belonging to the class Trebouxiophyceae.

8. The genetically modified strain of eukaryotic microalgae according to claim 7, wherein the genes are derived from a strain belonging to genus *Coccomyxa* or genus *Pseudococcomyxa*.

9. A method for producing TAG, comprising a step of culturing the genetically modified strain of eukaryotic microalgae according to claim 1.

* * * * *